(12) United States Patent
Rahman et al.

(10) Patent No.: US 7,833,693 B2
(45) Date of Patent: *Nov. 16, 2010

(54) PHOTOACTIVE COMPOUNDS

(75) Inventors: M. Dalil Rahman, Flemington, NJ (US);
Francis M. Houlihan, Millington, NJ (US); Munirathna Padmanaban, Bridgewater, NJ (US); SangHo Lee, Bridgewater, NJ (US); Ralph R. Dammel, Flemington, NJ (US); David Rentkiewicz, Roselle Park, NJ (US); Clement Anyadiegwu, Parlin, NJ (US)

(73) Assignee: AZ Electronic Materials USA Corp.

( * ) Notice: Subject to any disclaimer, the term of this patent is extended or adjusted under 35 U.S.C. 154(b) by 0 days.

This patent is subject to a terminal disclaimer.

(21) Appl. No.: 12/331,672

(22) Filed: Dec. 10, 2008

(65) Prior Publication Data

US 2009/0087782 A1    Apr. 2, 2009

Related U.S. Application Data

(60) Division of application No. 11/355,762, filed on Feb. 16, 2006, now Pat. No. 7,521,170, which is a continuation-in-part of application No. 11/179,886, filed on Jul. 12, 2005, now abandoned.

(51) Int. Cl.
*G03F 7/00* (2006.01)
*G03F 7/004* (2006.01)

(52) U.S. Cl. .................. 430/270.1; 430/913; 549/14; 549/30; 549/43; 549/44; 549/62; 549/63

(58) Field of Classification Search .............. 430/270.1, 430/913; 549/14, 30, 43, 44, 62, 83
See application file for complete search history.

(56) References Cited

U.S. PATENT DOCUMENTS

| | | | |
|---|---|---|---|
| 6,100,198 A | 8/2000 | Grieger et al. | |
| 6,358,665 B1 | 3/2002 | Pawlowski et al. | |
| 6,383,713 B1 | 5/2002 | Uetani et al. | |
| 6,548,221 B2 | 4/2003 | Uetani et al. | |
| 6,991,888 B2 | 1/2006 | Padmanaban et al. | |
| 7,189,492 B2 | 3/2007 | Kodama et al. | |
| 7,390,613 B1 | 6/2008 | Rahman et al. | |
| 7,491,482 B2 | 2/2009 | Padmanaban et al. | |
| 7,521,170 B2 | 4/2009 | Rahman et al. | |
| 7,678,528 B2 | 3/2010 | Rahman et al. | |
| 2005/0053861 A1 | 3/2005 | Yoneda et al. | |
| 2005/0266336 A1 | 12/2005 | Kodama | |
| 2008/0187868 A1 | 8/2008 | Padmanaban et al. | |

FOREIGN PATENT DOCUMENTS

| | | |
|---|---|---|
| DE | 295 421 A5 | 3/2005 |
| EP | 1 517 179 A1 | 3/2005 |
| EP | 1 566 692 A1 | 8/2005 |
| JP | 2005-92053 A | 4/2005 |
| JP | 2005-99456 A | 4/2005 |
| WO | WO 02/082185 A1 | 10/2002 |

OTHER PUBLICATIONS

Office Action dated Feb. 25, 2009 for U.S. Appl. No. 11/355,400.
Form PCT/IB/326, Form PCT/IB/373, and Form PCT/ISA/237 for PCT/IB2008/000317 dated Aug. 20, 2009, which corresponds to U.S. Appl. No. 11/672,077.
Notification of Transmittal of the International Search Report and the Written Opinion of the International Searching Authority, or the Declaration (Form PCT/ISA/220), International Search Report (Form PCT/ISA/210), and Written Opinion of the Searching Authority (Form PCT/ISA/237) for PCT/IB2006/003989 dated Aug. 25, 2009, which corresponds to U.S. Appl. No. 11/566,309.
Notice of Allowance, along with copy of allowed claims, from U.S. Appl. No. 11/355,400.
U.S. Appl. No. 11/179,886, filed Jul. 12, 2005.
U.S. Appl. No. 11/280,842, filed Nov. 16, 2005.

*Primary Examiner*—Amanda C. Walke
(74) *Attorney, Agent, or Firm*—Alan Kass; Sangya Jain

(57) ABSTRACT

The present application relates to a compound of formula A-X—B, where (i) A-X—B form an ionic compound Ai Xi Bi where Ai and Bi are each individually an organic onium cation; and Xi is anion of the formula $Q-R_{500}-SO_3^-$ or (ii) A-X—B form a non-ionic compound Ac-Xc-Bc, where Ai, Bi, Q, $R_{500}$, Ac, Bc, and Xc are defined herein. The compounds are useful as photoactive materials.

10 Claims, No Drawings

US 7,833,693 B2

PHOTOACTIVE COMPOUNDS

CROSS-REFERENCE TO RELATED APPLICATION

This application is a division application of Ser. No. 11/355,762, filed Feb. 16, 2006, now U.S. Pat. No. 7,521,170 which is a continuation-in-part application of Ser. No. 11/179,886, now abandoned filed Jul. 12, 2005, the contents of which are hereby incorporated herein by reference.

FIELD OF INVENTION

The present invention relates to novel photoactive compounds useful in photoresist compositions in the field of microlithography, and especially useful for imaging negative and positive patterns in the production of semiconductor devices, as well as photoresist compositions and processes for imaging photoresists.

BACKGROUND OF THE INVENTION

Photoresist compositions are used in microlithography processes for making miniaturized electronic components such as in the fabrication of computer chips and integrated circuits. Generally, in these processes, a thin coating of film of a photoresist composition is first applied to a substrate material, such as silicon wafers used for making integrated circuits. The coated substrate is then baked to evaporate any solvent in the photoresist composition and to fix the coating onto the substrate. The photoresist coated on the substrate is next subjected to an image-wise exposure to radiation.

The radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation exposed or the unexposed areas of the photoresist. The trend toward the miniaturization of semiconductor devices has led to the use of new photoresists that are sensitive at lower and lower wavelengths of radiation and has also led to the use of sophisticated multilevel systems to overcome difficulties associated with such miniaturization.

There are two types of photoresist compositions: negative-working and positive-working. The type of photoresist used at a particular point in lithographic processing is determined by the design of the semiconductor device. When negative-working photoresist compositions are exposed image-wise to radiation, the areas of the photoresist composition exposed to the radiation become less soluble to a developer solution (e.g. a cross-linking reaction occurs) while the unexposed areas of the photoresist coating remain relatively soluble to such a solution. Thus, treatment of an exposed negative-working resist with a developer causes removal of the non-exposed areas of the photoresist coating and the creation of a negative image in the coating, thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the creation of a positive image in the photoresist coating. Again, a desired portion of the underlying surface is uncovered.

Photoresist resolution is defined as the smallest feature, which the resist composition can transfer from the photomask to the substrate with a high degree of image edge acuity after exposure and development. In many leading edge manufacturing applications today, photoresist resolution on the order of less than one-half micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the push toward miniaturization reduces the critical dimensions on the devices. In cases where the photoresist dimensions have been reduced to below 150 nm, the roughness of the photoresist patterns has become a critical issue. Edge roughness, commonly known as line edge roughness, is typically observed for line and space patterns as roughness along the photoresist line, and for contact holes as side wall roughness. Edge roughness can have adverse effects on the lithographic performance of the photoresist, especially in reducing the critical dimension latitude and also in transferring the line edge roughness of the photoresist to the substrate. Hence, photoresists that minimize edge roughness are highly desirable.

Photoresists sensitive to short wavelengths, between about 100 nm and about 300 nm are often used where subhalfmicron geometries are required. Particularly preferred are photoresists comprising non-aromatic polymers, a photoacid generator, optionally a dissolution inhibitor, and solvent.

High resolution, chemically amplified, deep ultraviolet (100-300 nm) positive and negative tone photoresists are available for patterning images with less than quarter micron geometries. To date, there are three major deep ultraviolet (UV) exposure technologies that have provided significant advancement in miniaturization, and these use lasers that emit radiation at 248 nm, 193 nm and 157 nm. Photoresists used in the deep UV typically comprise a polymer which has an acid labile group and which can deprotect in the presence of an acid, a photoactive component which generates an acid upon absorption of light, and a solvent.

Photoresists for 248 nm have typically been based on substituted polyhydroxystyrene and its copolymers, such as those described in U.S. Pat. No. 4,491,628 and U.S. Pat. No. 5,350,660. On the other hand, photoresists for 193 nm exposure require non-aromatic polymers, since aromatics are opaque at this wavelength. U.S. Pat. No. 5,843,624 and GB 2,320,718 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon:hydrogen ratios which improve etch resistance, they also provide transparency at low wavelengths and they have relatively high glass transition temperatures. Photoresists sensitive at 157 nm have been based on fluorinated polymers, which are known to be substantially transparent at that wavelength. Photoresists derived from polymers containing fluorinated groups are described in WO 00/67072 and WO 00/17712.

The polymers used in a photoresist are designed to be transparent to the imaging wavelength, but on the other hand, the photoactive component has been typically designed to be absorbing at the imaging wavelength to maximize photosensitivity. The photosensitivity of the photoresist is dependent on the absorption characteristics of the photoactive component, the higher the absorption, the less the energy required to generate the acid, and the more photosensitive is the photoresist.

SUMMARY OF THE INVENTION

The present invention relates to a compound of the formula

A-X—B (i) where A-X—B form an ionic compound Ai Xi Bi, where Ai and Bi are each individually an organic onium cation; and Xi is anion of the formula

Q-$R_{500}$—$SO_3^-$ where Q is selected from $^-O_3S$ and $^-O_2C$; and $R_{500}$ is a group selected from linear or branched alkyl, cycloalkyl, aryl, or combinations thereof, optionally containing a catenary S or N, where the alkyl, cycloalkyl, and aryl groups are unsubstituted or substituted by one or more groups selected from the group consisting of halogen, unsubstituted or substituted alkyl, unsubstituted or substituted $C_{1-8}$ perfluoroalkyl, hydroxyl, cyano, sulfate, and nitro; and where the organic onium cation is selected from

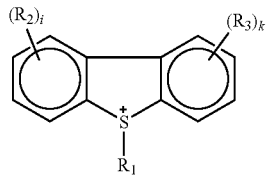

and

Y—Ar where Ar is selected from

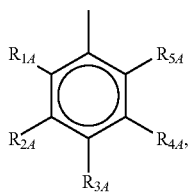

naphthyl, or anthryl;

Y is selected from

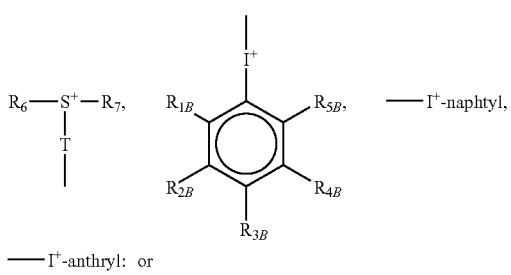

I⁺-anthryl: or (ii) where A-X—B form a non-ionic compound Ac-Xc-Bc, where Ac and Bc are each individually selected from

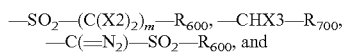

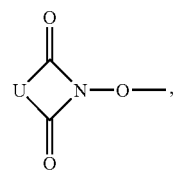

where $R_{600}$ is selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, or

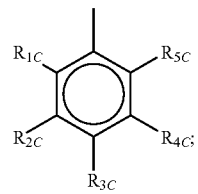

where $R_{700}$ is selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, or

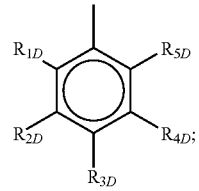

U is $C_1$ to $C_4$ unsubstituted or substituted alkylene;

Xc is

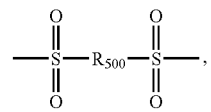

where $R_{500}$ is defined above;

where $R_1$, $R_2$, $R_3$, $R_{1A}$, $R_{1B}$, $R_{1C}$, $R_{2A}$, $R_{2B}$, $R_{2C}$, $R_{2D}$, $R_{3A}$, $R_{3B}$, $R_{3C}$, $R_{3D}$, $R_{4A}$, $R_{4B}$, $R_{4C}$, $R_{4D}$, $R_{5A}$, $R_{5B}$ and $R_{5C}$, are each independently selected from Z, hydrogen, $OSO_2R_9$, $OR_{20}$, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, arylcarbonylmethyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, straight or branched perfluoroalkyl, monocycloperfluoroalkyl or polycycloperfluoroalkyl, straight or branched alkoxy chain, nitro, cyano, halogen, carboxyl, hydroxyl, sulfate, tresyl, or hydroxyl; either (i) one of $R_{1D}$ or $R_{5D}$ is nitro with the other being selected from hydrogen, straight or branched alkyl chain optionally containing one or more O atoms, monocycloalkyl or polycycloalkyl group optionally containing one or more O atoms, monocycloalkyl or polycycloalkylcarbonyl group, aryl, aralkyl, straight or branched perfluoroalkyl, monocycloperfluoroalkyl or polycycloperfluoroalkyl, arylcarbonylmethyl group, cyano, or hydroxyl or (ii) both of $R_{1D}$ and $R_{5D}$ are nitro;

$R_6$ and $R_7$ are each independently selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, nitro, cyano, or hydroxyl or $R_6$ and $R_7$ together with the S atom to which they are attached form a 5-, 6-, or 7-membered saturated or unsaturated ring optionally containing one or more O atoms;

$R_9$ is selected from alkyl, fluoroalkyl, perfluoroalkyl, aryl, fluoroaryl, perfluoroaryl, monocycloalkyl or polycycloalkyl group with the cycloalkyl ring optionally containing one or more O atoms, monocyclofluoroalkyl or polycyclofluoroalkyl group with the cycloalkyl ring optionally containing one or more O atoms, or monocycloperfluoralkyl or polycycloperfluoroalkyl group with the cycloalkyl ring optionally containing one or more O atoms;

$R_{20}$ is alkoxyalkyl, alkoxycarbonylalkyl, alkylcarbonyl, monocycloalkyl- or polycycloalkyloxycarbonylalkyl with the cycloalkyl ring optionally containing one or more O atoms, or monocycloalkyl- or polycycloalkyloxyalkyl with the cycloalkyl ring optionally containing one or more O atoms;

T is a direct bond, a divalent straight or branched alkyl group optionally containing one or more O atoms, divalent aryl, divalent aralkyl, or divalent monocycloalkyl or polycycloalkyl group optionally containing one or more O atoms;

Z is $-(V)_j-(C(X11)(X12))_n-O-C(=O)-R_8$, where either (i) one of X11 or X12 is straight or branched alkyl chain containing at least one fluorine atom and the other is hydrogen, halogen, or straight or branched alkyl chain or (ii) both of X11 and X12 are straight or branched alkyl chain containing at least one fluorine atom;

V is a linkage group selected from a direct bond, a divalent straight or branched alkyl group optionally containing one or more O atoms, divalent aryl group, divalent aralkyl group, or divalent monocycloalkyl or polycycloalkyl group optionally containing one or more O atoms;

X2 is hydrogen, halogen, or straight or branched alkyl chain optionally containing one or more O atoms;

$R_8$ is a straight or branched alkyl chain optionally containing one or more O atoms, a monocycloalkyl or polycycloalkyl group optionally containing one or more O atoms, or aryl;

X3 is hydrogen, straight or branched alkyl chain, halogen, cyano, or $-C(=O)-R_{50}$ where $R_{50}$ is selected from straight or branched alkyl chain optionally containing one or more O atoms or $-O-R_{51}$ where $R_{51}$ is hydrogen or straight or branched alkyl chain;

each of i and k are independently 0 or a positive integer;

j is 0 to 10;

m is 0 to 10;

and n is 0 to 10, the alkyl, straight or branched alkyl chain optionally containing one or more O atoms, straight or branched alkyl chain, straight or branched alkoxy chain, monocycloalkyl or polycycloalkyl group optionally containing one or more O atoms, monocycloalkyl- or polycycloalkylcarbonyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, aralkyl, aryl, naphthyl, anthryl, 5-, 6-, or 7-membered saturated or unsaturated ring optionally containing one or more O atoms, or arylcarbonylmethyl group being unsubstituted or substituted by one or more groups selected from the group consisting of Z, halogen, alkyl, $C_{1-8}$ perfluoroalkyl, monocycloalkyl or polycycloalkyl group, $OR_{20}$, alkoxy, $C_{3-20}$ cyclic alkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

(II)

(III)

(IV)

(V)

(VI)

wherein $R_{10}$ and $R_{11}$ each independently represent a hydrogen atom, a straight or branched alkyl chain optionally containing one or more O atoms, or a monocycloalkyl or polycycloalkyl group optionally containing one or more O atoms, or $R_{10}$ and $R_{11}$ together can represent an alkylene group to form a five- or six-membered ring;

$R_{12}$ represents a straight or branched alkyl chain optionally containing one or more O atoms, a monocycloalkyl or polycycloalkyl group optionally containing one or more O atoms, or aralkyl, or $R_{10}$ and $R_{12}$ together represent an alkylene group which forms a five- or six-membered ring together with the interposing —C—O— group, the carbon atom in the ring being optionally substituted by an oxygen atom;

R$_{13}$ represents a straight or branched alkyl chain optionally containing one or more O atoms or a monocycloalkyl or polycycloalkyl group optionally containing one or more O atoms;

R$_{14}$ and R$_{15}$ each independently represent a hydrogen atom, a straight or branched alkyl chain optionally containing one or more O atoms or a monocycloalkyl or polycycloalkyl group optionally containing one or more O atoms;

R$_{16}$ represents a straight or branched alkyl chain optionally containing one or more O atoms, a monocycloalkyl or polycycloalkyl group optionally containing one or more O atoms, aryl, or aralkyl; and R$_{17}$ represents straight or branched alkyl chain optionally containing one or more O atoms, a monocycloalkyl or polycycloalkyl group optionally containing one or more O atoms, aryl, aralkyl, the group —Si(R$_{16}$)$_2$R$_{17}$, or the group —O—Si(R$_{16}$)$_2$R$_{17}$, the straight or branched alkyl chain optionally containing one or more O atoms, monocycloalkyl or polycycloalkyl group optionally containing one or more O atoms, aryl, and aralkyl being unsubstituted or substituted as above.

The compound A-X—B where A-X—B is the ionic compound Ai Xi Bi is preferred.

The present invention also relates to a photoresist composition comprising a polymer containing an acid labile group and a compound as described above.

The photoresist composition can optionally contain a second photoacid generator having the formula Ai Xi1 where Ai is as defined above and Xi1 is an anion selected from CF$_3$SO$_3^-$, CHF$_2$SO$_3^-$, CH$_3$SO$_3^-$, CCl$_3$SO$_3^-$, C$_2$F$_5$SO$_3^-$, C$_2$HF$_4$SO$_3^-$, C$_4$F$_9$SO$_3^-$, camphor sulfonate, perfluorooctane sulfonate, benzene sulfonate, pentafluorobenzene sulfonate, toluene sulfonate, perfluorotoluene sulfonate, (Rf1SO$_2$)$_3$C$^-$ and (Rf1SO$_2$)$_2$N$^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and Rg-O—Rf2—SO$_3^-$, where Rf2 is selected from the group consisting of linear or branched (CF$_2$)$_j$ where j is an integer from 4 to 10 and C$_1$-C$_{12}$ cycloperfluoroalkyl divalent radical which is optionally perfluoroC$_{1-10}$alkyl substituted, Rg is selected from the group consisting of C$_1$-C$_{20}$ linear, branched, monocycloalkyl or polycycloalkyl, C$_1$-C$_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated. Examples of such anions Xi1 include (C$_2$F$_5$SO$_2$)$_2$N$^-$, (C$_4$F$_9$SO$_2$)$_2$N$^-$, (C$_8$F$_{17}$SO$_2$)$_3$C$^-$, (CF$_3$SO$_2$)$_3$C$^-$, (CF$_3$SO$_2$)$_2$N$^-$, (CF$_3$SO$_2$)$_2$(C$_4$F$_9$SO$_2$)C$^-$, (C$_2$F$_5$SO$_2$)$_3$C$^-$, (C$_4$F$_9$SO$_2$)$_3$C$^-$, (CF$_3$SO$_2$)$_2$(C$_2$F$_5$SO$_2$)C$^-$, (C$_4$F$_9$SO$_2$)(C$_2$F$_5$SO$_2$)$_2$C$^-$, (CF$_3$SO$_2$)(C$_4$F$_9$SO$_2$)N$^-$, [(CF$_3$)$_2$NC$_2$F$_4$SO$_2$]$_2$N$^-$, (CF$_3$)$_2$NC$_2$F$_4$SO$_2$C$^-$(SO$_2$CF$_3$)$_2$, (3,5-bis(CF$_3$)C$_6$H$_3$)SO$_2$N$^-$SO$_2$CF$_3$, C$_6$F$_5$SO$_2$C$^-$(SO$_2$CF$_3$)$_2$, C$_6$F$_5$SO$_2$N$^-$SO$_2$CF$_3$,

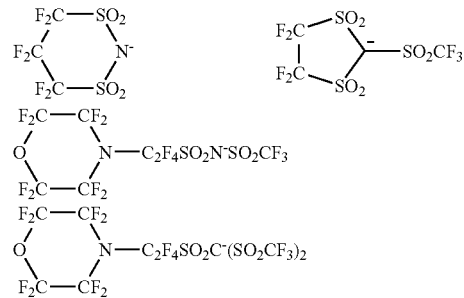

CF$_3$CHFO(CF$_2$)$_4$SO$_3^-$, CF$_3$CH$_2$O(CF$_2$)$_4$SO$_3^-$, CH$_3$CH$_2$O(CF$_2$)$_4$SO$_3^-$, CH$_3$CH$_2$CH$_2$O(CF$_2$)$_4$SO$_3^-$, CH$_3$O(CF$_2$)$_4$SO$_3^-$, C$_2$H$_5$O(CF$_2$)$_4$SO$_3^-$, C$_4$H$_9$O(CF$_2$)$_4$SO$_3^-$, C$_6$H$_5$CH$_2$O(CF$_2$)$_4$SO$_3^-$, C$_2$H$_5$OCF$_2$CF(CF$_3$)SO$_3^-$, CH$_2$=CHCH$_2$O(CF$_2$)$_4$SO$_3^-$, CH$_3$OCF$_2$CF(CF$_3$)SO$_3^-$, C$_4$H$_9$OCF$_2$CF(CF$_3$)SO$_3^-$, C$_8$H$_{17}$O(CF$_2$)$_2$SO$_3^-$, and C$_4$H$_9$O(CF$_2$)$_2$SO$_3^-$. Other examples of suitable anions can be found in U.S. Pat. No. 6,841,333 and U.S. Pat. No. 5,874,616.

Examples of Ai Xi1 include bis(4-t-butylphenyl iodonium) bis-perfluoroethane sulfonamide, diphenyliodonium trifluoromethane sulfonate, diphenyliodonium nonafluorobutane sulfonate, triphenylsulfonium trifluoromethane sulfonate, triphenylsulfonium nonafluorobutane sulfonate and the like as well as other photoacid generators known to those skilled in the art.

DETAILED DESCRIPTION OF THE INVENTION

The present invention relates to a compound of the formula

(i) where A-X—B form an ionic compound Ai Xi Bi, where Ai and Bi are each individually an organic onium cation; and Xi is anion of the formula

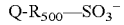

where Q is selected from $^-$O$_3$S and $^-$O$_2$C; and

R$_{500}$ is a group selected from linear or branched alkyl, cycloalkyl, aryl, or combinations thereof, optionally containing a catenary S or N, where the alkyl, cycloalkyl, and aryl groups are unsubstituted or substituted by one or more groups selected from the group consisting of halogen, unsubstituted or substituted alkyl, unsubstituted or substituted C$_{1-8}$ perfluoroalkyl, hydroxyl, cyano, sulfate, and nitro; and where the organic onium cation is selected from

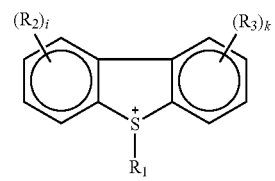

and

where Ar is selected from

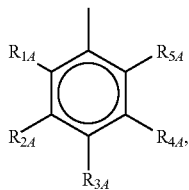

naphthyl, or anthryl;

Y is selected from

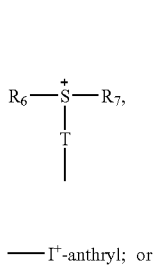 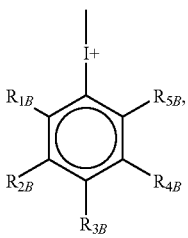 —I⁺-naphtyl,

—I⁺-anthryl; or (ii) where A-X—B form a non-ionic compound Ac-Xc-Bc, where Ac and Bc are each individually selected from

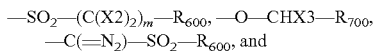

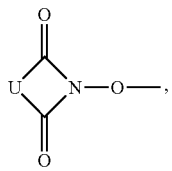

where $R_{600}$ is selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, or

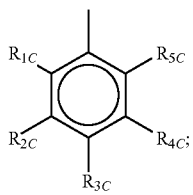

where $R_{700}$ is selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, or

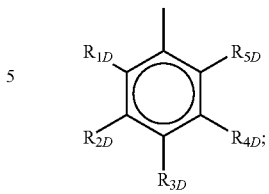

U is $C_1$ to $C_4$ unsubstituted or substituted alkylene;

Xc is

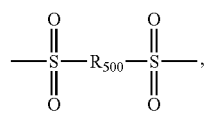

where $R_{500}$ is defined above;

where $R_1$, $R_2$, $R_3$, $R_{1A}$, $R_{1B}$, $R_{1C}$, $R_{2A}$, $R_{2B}$, $R_{2C}$, $R_{2D}$, $R_{3A}$, $R_{3B}$, $R_{3C}$, $R_{3D}$, $R_{4A}$, $R_{4B}$, $R_{4C}$, $R_{4D}$, $R_{5A}$, $R_{5B}$ and $R_{5C}$, are each independently selected from Z, hydrogen, $OSO_2R_9$, $OR_{20}$, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, arylcarbonylmethyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, straight or branched perfluoroalkyl, monocycloperfluoroalkyl or polycycloperfluoroalkyl, straight or branched alkoxy chain, nitro, cyano, halogen, carboxyl, hydroxyl, sulfate, tresyl, or hydroxyl; either (i) one of $R_{1D}$ or $R_{5D}$ is nitro with the other being selected from hydrogen, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, cyano, or hydroxyl or (ii) both of $R_{1D}$ and $R_{5D}$ are nitro;

$R_6$ and $R_7$ are each independently selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, nitro, cyano, or hydroxyl or $R_6$ and $R_7$ together with the S atom to which they are attached form a 5-, 6-, or 7-membered saturated or unsaturated ring optionally containing one or more O atoms;

$R_9$ is selected from alkyl, fluoroalkyl, perfluoroalkyl, aryl, fluoroaryl, perfluoroaryl, monocycloalkyl or polycycloalkyl group with the cycloalkyl ring optionally containing one or more O atoms, monocyclofluoroalkyl or polycyclofluoroalkyl group with the cycloalkyl ring optionally containing one or more O atoms, or monocycloperfluoralkyl or polycycloperfluoroalkyl group with the cycloalkyl ring optionally containing one or more O atoms;

$R_{20}$ is alkoxyalkyl, alkoxycarbonylalkyl, alkylcarbonyl, monocycloalkyl- or polycycloalkyloxycarbonylalkyl with the cycloalkyl ring optionally containing one or more O atoms, or monocycloalkyl- or polycycloalkyloxyalkyl with the cycloalkyl ring optionally containing one or more O atoms;

T is a direct bond, a divalent straight or branched alkyl group optionally containing one or more O atoms, divalent aryl group, divalent aralkyl group, or divalent monocycloalkyl or polycycloalkyl group optionally containing one or more O atoms;

Z is $-(V)_j-(C(X11)(X12))_n-O-C(=O)-R_8$, where either (i) one of X11 or X12 is straight or branched alkyl chain containing at least one fluorine atom and the other is hydrogen, halogen, or straight or branched alkyl chain or (ii) both of X11 and X12 are straight or branched alkyl chain containing at least one fluorine atom;

V is a linkage group selected from a direct bond, a divalent straight or branched alkyl group optionally containing one or more O atoms, divalent aryl group, divalent aralkyl group, or divalent monocycloalkyl or polycycloalkyl group optionally containing one or more O atoms;

X2 is hydrogen, halogen, or straight or branched alkyl chain optionally containing one or more O atoms;

$R_8$ is a straight or branched alkyl chain optionally containing one or more O atoms, a monocycloalkyl or polycycloalkyl group optionally containing one or more O atoms, or aryl;

X3 is hydrogen, straight or branched alkyl chain, halogen, cyano, or $-C(=O)-R_{50}$ where $R_{50}$ is selected from straight or branched alkyl chain optionally containing one or more O atoms or $-O-R_{51}$ where $R_{51}$ is hydrogen or straight or branched alkyl chain;

each of i and k are independently 0 or a positive integer;

j is 0 to 10;

m is 0 to 10;

and n is 0 to 10, the alkyl, straight or branched alkyl chain optionally containing one or more O atoms, straight or branched alkyl chain, straight or branched alkoxy chain, monocycloalkyl or polycycloalkyl group optionally containing one or more O atoms, monocycloalkyl- or polycycloalkylcarbonyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, aralkyl, aryl, naphthyl, anthryl, 5-, 6-, or 7-membered saturated or unsaturated ring optionally containing one or more O atoms, or arylcarbonylmethyl group being unsubstituted or substituted by one or more groups selected from the group consisting of Z, halogen, alkyl, $C_{1-8}$ perfluoroalkyl, monocycloalkyl or polycycloalkyl group, $OR_{20}$, alkoxy, $C_{3-20}$ cyclic alkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

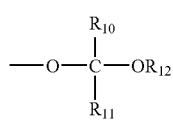
(II)

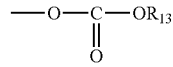
(III)

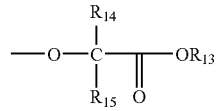
(IV)

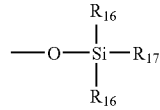
(V)

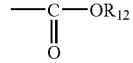
(VI)

wherein $R_{10}$ and $R_{11}$ each independently represent a hydrogen atom, a straight or branched alkyl chain optionally containing one or more O atoms, or a monocycloalkyl or polycycloalkyl group optionally containing one or more O atoms, or $R_{10}$ and $R_{11}$ together can represent an alkylene group to form a five- or six-membered ring;

$R_{12}$ represents a straight or branched alkyl chain optionally containing one or more O atoms, a monocycloalkyl or polycycloalkyl group optionally containing one or more O atoms, or aralkyl, or $R_{10}$ and $R_{12}$ together represent an alkylene group which forms a five- or six-membered ring together with the interposing $-C-O-$ group, the carbon atom in the ring being optionally substituted by an oxygen atom;

$R_{13}$ represents a straight or branched alkyl chain optionally containing one or more O atoms or a monocycloalkyl or polycycloalkyl group optionally containing one or more O atoms;

$R_{14}$ and $R_{15}$ each independently represent a hydrogen atom, a straight or branched alkyl chain optionally containing one or more O atoms or a monocycloalkyl or polycycloalkyl group optionally containing one or more O atoms;

$R_{16}$ represents a straight or branched alkyl chain optionally containing one or more O atoms, a monocycloalkyl or polycycloalkyl group optionally containing one or more O atoms, aryl, or aralkyl; and $R_{17}$ represents straight or branched alkyl chain optionally containing one or more O atoms, a monocycloalkyl or polycycloalkyl group optionally containing one or more O atoms, aryl, aralkyl, the group $-Si(R_{16})_2R_{17}$, or the group $-O-Si(R_{16})_2R_{17}$, the straight or branched alkyl chain optionally containing one or more O atoms, monocycloalkyl or polycycloalkyl group optionally containing one or more O atoms, aryl, and aralkyl being unsubstituted or substituted as above.

The compound A-X-B where A-X-B is the ionic compound Ai Xi Bi is preferred.

The present invention also relates to a photoresist composition comprising a polymer containing an acid labile group and a compound as described above.

The photoresist composition can optionally contain a second photoacid generator having the formula Ai Xi1 where Ai is as defined above and Xi1 is an anion selected from $CF_3SO_3^-$, $CHF_2SO_3^-$, $CH_3SO_3^-$, $CCl_3SO_3^-$, $C_2F_5SO_3^-$, $C_2HF_4SO_3^-$, $C_4F_9SO_3^-$, camphor sulfonate, perfluorooctane sulfonate, benzene sulfonate, pentafluorobenzene sulfonate, toluene sulfonate, perfluorotoluene sulfonate, $(Rf1SO_2)_3C^-$ and $(Rf1SO_2)_2N^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and Rg-O—Rf2—SO$_3$-, where Rf2 is selected from the group consisting of linear or branched $(CF_2)_j$ where j is an integer from 4 to 10 and $C_1$-$C_{12}$ cycloperfluoroalkyl divalent radical which is optionally perfluoro$C_{1-10}$alkyl substituted, Rg is selected from the group consisting of $C_1$-$C_{20}$ linear, branched, monocycloalkyl or polycycloalkyl, $C_1$-$C_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated. Examples of such anions Xi1 include $(C_2F_5SO_2)_2N^-$, $(C_4F_9SO_2)_2N^-$, $(C_8F_{17}SO_2)_3C^-$, $(C F_3SO_2)_3C^-$, $(CF_3SO_2)_2N^-$, $(CF_3SO_2)_2(C_4F_9SO_2)C^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)(C_4F_9SO_2)N^-$, $[(CF_3)_2NC_2F_4SO_2]_2N^-$, $(CF_3)_2NC_2F_4SO_2C^-(SO_2CF_3)_2$, $(3,5-bis(CF_3)C_6H_3)SO_2N^-SO_2CF_3$, $C_6F_5SO_2C^-(SO_2CF_3)_2$, $C_6F_5SO_2N^-SO_2CF_3$,

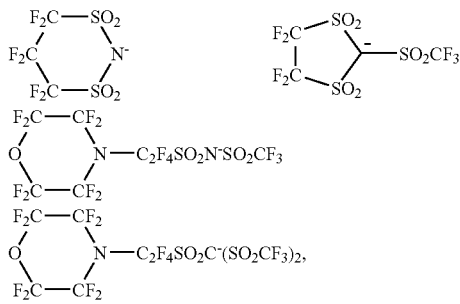

$CF_3CHFO(CF_2)_4SO_3^-$, $CF_3CH_2O(CF_2)_4SO_3^-$, $CH_3CH_2O(CF_2)_4SO_3^-$, $CH_3CH_2CH_2O(CF_2)_4SO_3^-$, $CH_3O(CF_2)_4SO_3^-$, $C_2H_5O(CF_2)_4SO_3^-$, $C_4H_9O(CF_2)_4SO_3^-$, $C_6H_5CH_2O(CF_2)_4SO_3^-$, $C_2H_5OCF_2CF(CF_3)SO_3^-$, $CH_2=CHCH_2O(CF_2)_4SO_3^-$, $CH_3OCF_2CF(CF_3)SO_3^-$, $C_4H_9OCF_2CF(CF_3)SO_3^-$, $C_8H_{17}O(CF_2)_2SO_3^-$, and $C_4H_9O(CF_2)_2SO_3^-$. Other examples of suitable anions can be found in U.S. Pat. No. 6,841,333 and U.S. Pat. No. 5,874,616.

Examples of Ai Xi1 include bis(4-t-butylphenyl iodonium) bis-perfluoroethane sulfonamide, diphenyliodonium trifluoromethane sulfonate, diphenyliodonium nonafluorobutane sulfonate, triphenylsulfonium trifluoromethane sulfonate, triphenylsulfonium nonafluorobutane sulfonate and the like as well as other photoacid generators known to those skilled in the art.

The term alkyl as used herein means a straight or branched chain hydrocarbon. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

Alkylene refers to divalent alkyl radicals, which can be linear or branched, such as, for example, methylene, ethylene, propylene, butylene or the like.

By the term aryl is meant a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthryl, phenanthryl, and the like. The aryl group can be unsubstituted or substituted as provided for hereinabove.

The term alkoxy refers to a group of alkyl-O—, where alkyl is defined herein. Representative examples of alkoxy include, but are not limited to, methoxy, ethoxy, propoxy, 2-propoxy, butoxy, tert-butoxy, pentyloxy, and hexyloxy.

The term aryloxy refers to a group of arykl-O—, where aryl is defined herein.

By the term aralkyl is meant an alkyl group containing an aryl group. It is a hydrocarbon group having both aromatic and aliphatic structures, that is, a hydrocarbon group in which a lower alkyl hydrogen atom is substituted by a mononuclear or polynuclear aryl group. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, naphthylmethyl, and the like.

The term monocycloalkyl as used herein, refers to an optionally substituted, saturated or partially unsaturated monocycloalkyl ring system, where if the ring is partially unsaturated, it is then a monocycloalkenyl group. The term polycycloalkyl as used herein refers to an optionally substituted, saturated or partially unsaturated polycycloalkyl ring system containing two or more rings, where if the ring is partially unsaturated, it is then a polycycloalkenyl group. Examples of monocycloalkyl or polycycloalkyl groups optionally containing one or more O atoms are well know to those skilled in the art and include, for example, cyclopropyl, cyclobutyl, cyclopentyl, cycloheptyl, cyclohexyl, 2-methyl-2-norbornyl, 2-ethyl-2-norbornyl, 2-methyl-2-isobornyl, 2-ethyl-2-isobornyl, 2-methyl-2-adamantyl, 2-ethyl-2-adamantyl, 1-adamantyl-1-methylethyl, adamantyl, tricyclodecyl, 3-oxatricyclo[4.2.1.0$^{2,5}$]nonyl, tetracyclododecanyl, tetracyclo[5.2.2.0.0]undecanyl, bornyl, isobornyl norbornyl lactone, adamantyl lactone and the like.

The term alkoxycarbonylalkyl embraces alkyl radicals substituted with an alkoxycarbonyl radical as defined herein. Examples of alkoxycarbonylalkyl radicals include methoxycarbonylmethyl [$CH_3O$—$C(=O)$—$CH_2$—], ethoxycarbonylmethyl [$CH_3CH_2O$—$C(=O)CH_2$], methoxycarbonylethyl [$CH_3O$—$C(=O)$—$CH_2CH_2$—], and ethoxycarbonylethyl [$CH_3CH_2O$—$C(=O)$—$CH_2CH_2$].

The term alkylcarbonyl as used herein means an alkyl group, as defined herein, appended to the parent molecular moiety through a carbonyl group, as defined herein, which can be generically represented as alkyl-C(O)—. Representative examples of alkylcarbonyl include, but are not limited to acetyl (methyl carbonyl), butyryl (propylcarbonyl), octanoyl (heptylcarbonyl), dodecanoyl (undecylcarbonyl), and the like.

Alkoxycarbonyl means alkyl-O—C(O)—, wherein alkyl is as previously described. Non-limiting examples include methoxycarbonyl [$CH_3O$—$C(O)$—] and the ethoxycarbonyl [$CH_3CH_2O$—$C(O)$—], benzyloxycarbonyl [$C_6H_5CH_2O$—$C(O)$—] and the like.

Alkoxyalkyl means that a terminal alkyl group is linked through an ether oxygen atom to an alkyl moiety, which can be generically represented as alkyl-O-alkyl wherein the alkyl groups can be linear or branched. Examples of alkoxyalkyl include, but are not limited to, methoxypropyl, methoxybutyl, ethoxypropyl, methoxymethyl Monocycloalkyl- or polycycloalkyloxycarbonylalkyl means that a terminal monocycloalkyl or polycycloalkyl group is linked through —O—C(=O)— to an alkyl moiety, generically represented as monocycloalkyl- or polycycloalkyl —O—C(=O)-alkyl.

Monocycloalkyl- or polycycloalkyloxyalkyl means that a terminal monocycloalkyl or polycycloalkyl group is linked through an ether oxygen atom to an alkyl moiety, which can be generically represented as monocycloalkyl- or polycycloalkylalkyl.

Monocyclofluoroalkyl- or polycyclofluoroalkyl means a monocyclalkyl- or polycycloalkyl group substituted with one or more fluorine atoms.

Polymers useful in the photoresist compositions include those that have acid labile groups that make the polymer insoluble in aqueous alkaline solution, but such a polymer in the presence of an acid catalytically deprotects the polymer, wherein the polymer then becomes soluble in an aqueous alkaline solution. The polymers preferably are transparent below 200 nm, and are essentially non-aromatic, and preferably are acrylates and/or cycloolefin polymers. Such polymers are, for example, but not limited to, those described in U.S. Pat. No. 5,843,624, U.S. Pat. No. 5,879,857, WO 97/33, 198, EP 789,278 and GB 2,332,679. Nonaromatic polymers that are preferred for irradiation below 200 nm are substituted acrylates, cycloolefins, substituted polyethylenes, etc. Aromatic polymers based on polyhydroxystyrene and its copolymers may also be used, especially for 248 nm exposure.

Polymers based on acrylates are generally based on poly (meth)acrylates with at least one unit containing pendant alicyclic groups, and with the acid labile group being pendant from the polymer backbone and/or from the alicyclic group. Examples of pendant alicyclic groups, may be adamantyl, tricyclodecyl, isobornyl, menthyl and their derivatives. Other pendant groups may also be incorporated into the polymer, such as mevalonic lactone, gamma butyrolactone, alkyloxyalkyl, etc. Examples of structures for the alicyclic group include:

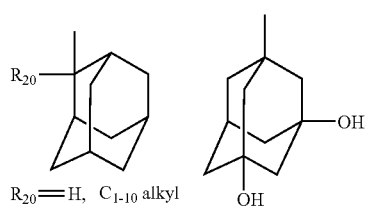

$R_{20}$=H, $C_{1-10}$ alkyl

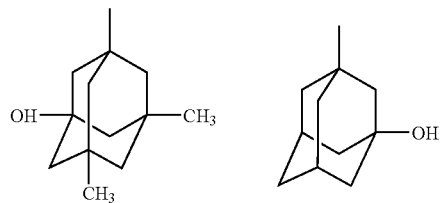

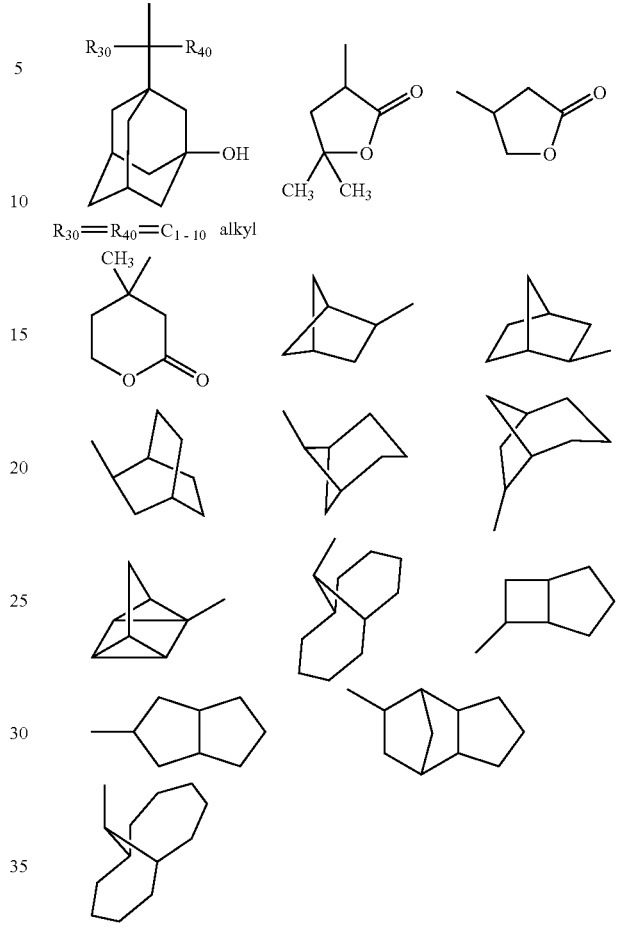

$R_{30}$=$R_{40}$=$C_{1-10}$ alkyl

The type of monomers and their ratios incorporated into the polymer are optimized to give the best lithographic performance. Such polymers are described in R. R. Dammel et al., Advances in Resist Technology and Processing, SPIE, Vol. 3333, p 144, (1998). Examples of these polymers include poly(2-methyl-2-adamantyl methacrylate-co-mevalonic lactone methacrylate), poly(carboxy-tetracyclododecyl methacrylate-co-tetrahydropyranylcarboxytetracyclododecyl methacrylate), poly(tricyclodecylacrylate-co-tetrahydropyranylmethacrylate-co-methacrylicacid), poly(3-oxocyclohexyl methacrylate-co-adamantylmethacrylate).

Polymers synthesized from cycloolefins, with norbornene and tetracyclododecene derivatives, may be polymerized by ring-opening metathesis, free-radical polymerization or using metal organic catalysts. Cycloolefin derivatives may also be copolymerized with cyclic anhydrides or with maleimide or its derivatives. Examples of cyclic anhydrides are maleic anhydride (MA) and itaconic anhydride. The cycloolefin is incorporated into the backbone of the polymer and may be any substituted or unsubstituted multicyclic hydrocarbon containing an unsaturated bond. The monomer can have acid labile groups attached. The polymer may be synthesized from one or more cycloolefin monomers having an unsaturated bond. The cycloolefin monomers may be substituted or unsubstituted norbornene, or tetracyclododecane. The substituents on the cycloolefin may be aliphatic or cycloaliphatic alkyls, esters, acids, hydroxyl, nitrile or alkyl derivatives. Examples of cycloolefin monomers, without limitation, include:

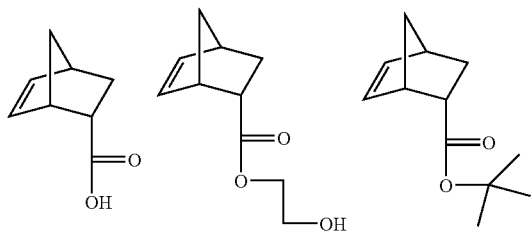

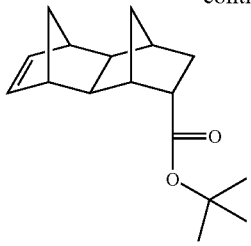

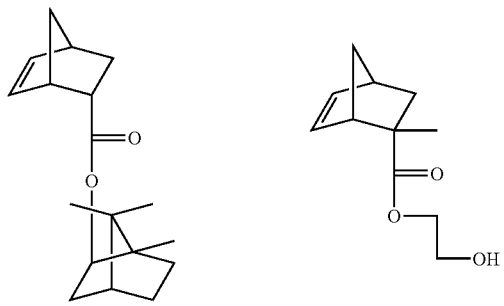

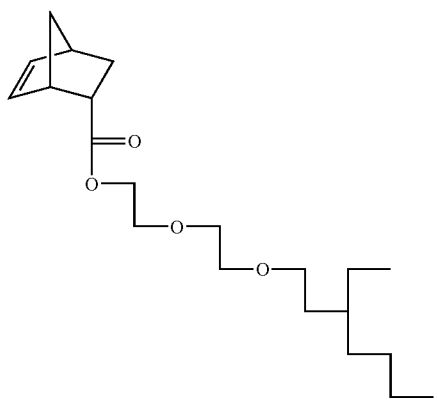

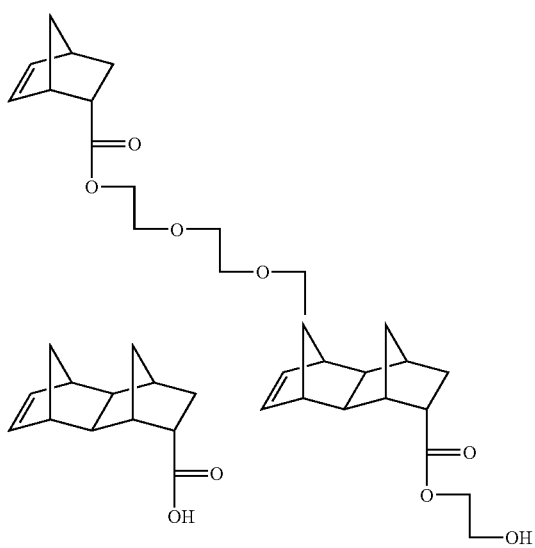

Other cycloolefin monomers which may also be used in synthesizing the polymer are:

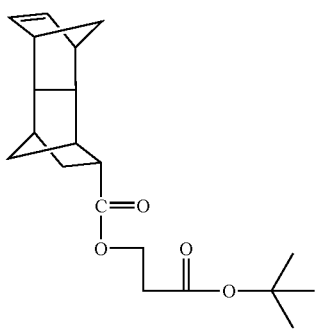

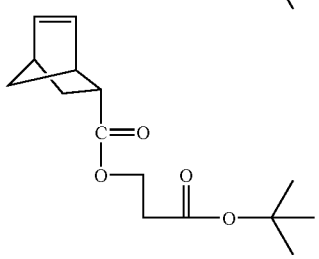

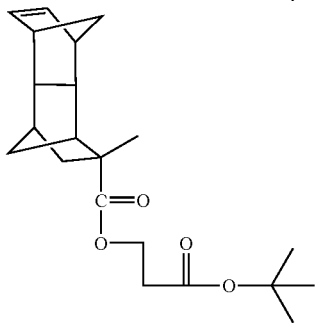

Such polymers are described in the following reference and incorporated herein, M-D. Rahman et al, Advances in Resist Technology and Processing, SPIE, Vol. 3678, p 1193, (1999). Examples of these polymers include poly((t-butyl-5-norbornene-2-carboxylate-co-2-hydroxyethyl-5-norbornene-2-carboxylate-co-5-norbornene-2-carboxylic acid-co-maleic anhydride), poly(t-butyl-5-norbornene-2-carboxylate-co-isobornyl-5-norbornene-2-carboxylate-co-2-hydroxyethyl-5-norbornene-2-carboxylate-co-5-norbornene-2-carboxylic acid-co-maleic anhydride), poly(tetracyclododecene-5-carboxylate-co-maleic anhydride), poly(t-butyl-5-norbornene-2-carboxylate-o-maleic anhydride-co-2-methyladamantyl methacrylate-co-2-mevalonic lactone methacrylate), poly(2-methyladamantyl methacrylate-co-2-mevalonic lactone methacylate) and the like.

Polymers containing mixtures of (meth)acrylate monomers, cycloolefinic monomers and cyclic anhydrides, where such monomers are described above, may also be combined into a hybrid polymer. Examples of cycloolefin monomers include those selected from t-butyl norbornene carboxylate (BNC), hydroxyethyl norbornene carboxylate (HNC), norbornene carboxylic acid (NC), t-butyltetracyclo[4.4.0.1.$^{2,6}$1.$^{7,10}$]dodec-8-ene-3-carboxylate, and t-butoxy carbonylmethyl tetracyclo[4.4.0.1.$^{2,6}$1.$^{7,10}$]dodec-8-ene-3-carboxylate. In some instances, preferred examples of cycloolefins include t-butyl norbornene carboxylate (BNC), hydroxyethyl norbornene carboxylate (HNC), and norbornene carboxylic acid (NC). Examples of (meth)acrylate monomers include those selected from mevalonic lactone methacrylate (MLMA), 2-methyl-2-adamantyl methacrylate (MAdMA), 2-adamantyl methacrylate (AdMA), 2-methyl-2-adamantyl acrylate (MAdA), 2-ethyl-2-adamantyl methacrylate (EAdMA), 3,5-dimethyl-7-hydroxy adamantyl methacrylate (DMHAdMA), isoadamantyl methacrylate, hydroxy-1-methacryloxyadamatane (HAdMA; for example, hydroxy at the 3-position), hydroxy-1-adamantyl acrylate (HADA; for example, hydroxy at the 3-position), ethylcyclopentylacrylate (ECPA), ethylcyclopentylmethacrylate (ECPMA), tricyclo[5,2,1,0$^{2,6}$]deca8-yl methacrylate (TCDMA), 3,5-dihydroxy-1-methacryloxyadamantane (DHAdMA), β-methacryloxy-γ-butyrolactone, α- or β-gamma-butyrolactone methacrylate (either α- or β-GBLMA), 5-methacryloyloxy-2,6-norbornanecarbolactone (MNBL), 5-acryloyloxy-2,6-norbornanecarbolactone (ANBL), isobutyl methacrylate (IBMA), α-gamma-butyrolactone acrylate (α-GBLA), spirolactone (meth)acrylate, oxytricyclodecane (meth)acrylate, adamantane lactone (meth)acrylate, and α-methacryloxy-γ-butyrolactone, among others. Examples of polymers formed with these monomers include poly(2-methyl-2-adamantyl methacrylate-co-2-ethyl-2-adamantyl methacrylate-co-3-hydroxy-1-methacryloxyadamantane-co-α-gamma-butyrolactone methacrylate); poly(2-ethyl-2-adamantyl methacrylate-co-3-hydroxy-1-methacryloxyadamantane-co-β-gamma-butyrolactone methacrylate); poly(2-methyl-2-adamantyl methacrylate-co-3-hydroxy-1-methacryloxyadamantane-co-β-gamma-butyrolactone methacrylate); poly(t-butyl norbornene carboxylate-co-maleic anhydride-co-2-methyl-2-adamantyl methacrylate-co-β-gamma-butyrolactone methacrylate-co-methacryloyloxy norbornene methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca8-yl methacrylate); poly(2-ethyl-2-adamantyl methacrylate-co-3-hydroxy-1-adamantyl acrylate-co-β-gamma-butyrolactone methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca8-yl methacrylate); poly(2-methyl-2-adamantyl methacrylate-co-3,5-dihydroxy-1-methacryloxyadamantane-co-α-gamma-butyrolactone methacrylate); poly(2-methyl-2-adamantyl methacrylate-co-3,5-dimethyl-7-hydroxy adamantyl methacrylate-co-α-gamma-butyrolactone methacrylate); poly(2-methyl-2-adamantyl acrylate-co-3-hydroxy-1-methacryloxyadamantane-co-α-gamma-butyrolactone methacrylate); poly(2-methyl-2-adamantyl methacrylate-co-3-hydroxy-1-methacryloxyadamantane-co-β-gamma-butyrolactone methacrylate-co-tricyclo[5,2,1,$^{2,6}$]deca-8-yl methacrylate); poly(2-methyl-2-adamantyl methacrylate co-β-gamma-butyrolactone methacrylate-co-3-hydroxy-1-methacryloxyadamantane-co-ethylcyclopentylacrylate); poly(2-methyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-methacryloxyadamantane-co-α-gamma-butyrolactone methacrylate-co-2-ethyl-2-adamantyl methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca8-yl methacrylate); poly(2-methyl-2-adamantyl methacrylate-co-2-ethyl-2-adamantyl methacrylate-co-β-gamma-butyrolactone methacrylate-co-3-hydroxy-1-methacryloxyadamantane); poly(2-methyl-2-adamantyl methacrylate-co-2-ethyl-2-adamantyl methacrylate-co-α-gamma-butyrolactone methacrylate-co-3-hydroxy-1-methacryloxyadamantane); poly(2-methyl-2-adamantyl methacrylate-co-methacryloyloxy norbornene methacrylate-co-β-gamma-butyrolactone methacrylate); poly(ethylcyclopentylmethacrylate-co-2-ethyl-2-adamantyl methacrylate-co-α-gamma-butyrolactone acrylate); poly(2-ethyl-2-adamantyl methacrylate-co-3-hydroxy-1-adamantyl acrylate-co-isobutyl methacrylate-co-α-gamma-butyrolactone acrylate); poly(2-methyl-2-adamantyl methacrylate-co-β-gamma-butyrolactone methacrylate-co-3-hydroxy-1-adamantyl acrylate-co-tricyclo[5,2, 1,02,6]deca-8-yl methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-βgamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-β-gamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-tricyclo[5,2, 1,02,6]deca-8-yl methacrylate-co-3-hydroxy-1-methacryloxyadamatane-co-α-gamma-butyrolactone methacrylate); poly(2-ethyl-2-adamantyl methacrylate-co-3-hydroxy-1-adamantyl acrylate-co-tricyclo[5,2,1,02,6]deca-8-yl methacrylate-co-α-gamma-butyrolactone methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-3-hydroxy-1-methacryloxyadamatane-co-α-gamma-butyrolactone methacrylate-co-2-ethyl-2-adamantyl-co-methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-adamantyl acrylate-co-5-acryloyloxy-2,6-norbornanecarbolactone); poly(2-ethyl-2-adamantyl methacrylate-co-3-hydroxy-1-adamantyl acrylate-co-α-gamma-butyrolactone methacrylate-co-α-gamma-butyrolactone acrylate); poly(2-ethyl-2-adamantyl methacrylate-co-3-hydroxy-1-adamantyl acrylate-co-α-gamma-butyrolactone methacrylate-co-2-adamantyl methacrylate); and poly(2-ethyl-2-adamantyl methacrylate-co-3-hydroxy-1-adamantyl acrylate-co-α-gamma-butyrolactone acrylate-co-tricyclo[5, 2,1,02,6]deca-8-yl methacrylate).

Other examples of suitable polymers include those described in U.S. Pat. Nos. 6,610,465, 6,120,977, 6,136,504, 6,013,416, 5,985,522, 5,843,624, 5,693,453, 4,491,628, WO 00/25178, WO 00/67072, JP 2000-275845, JP 2000-137327, and JP 09-73173 which are incorporated herein by reference. Blends of one or more photoresist resins may be used. Standard synthetic methods are typically employed to make the various types of suitable polymers. Procedures or references to suitable standard procedures (e.g., free radical polymerization) can be found in the aforementioned documents.

The cycloolefin and the cyclic anhydride monomer are believed to form an alternating polymeric structure, and the amount of the (meth)acrylate monomer incorporated into the polymer can be varied to give the optimal lithographic properties. The percentage of the (meth)acrylate monomer relative to the cycloolefin/anhydride monomers within the polymer ranges from about 95 mole % to about 5 mole %, further ranging from about 75 mole % to about 25 mole %, and also further ranging from about 55 mole % to about 45 mole %.

Fluorinated non-phenolic polymers, useful for 157 nm exposure, also exhibit line edge roughness and can benefit from the use of the novel mixture of photoactive compounds described in the present invention. Such polymers are described in WO 00/17712 and WO 00/67072 and incorporated herein by reference. Example of one such polymer is poly(tetrafluoroethylene-co-norbornene-co-5-hexafluoroisopropanol-substituted 2-norbornene.

Polymers synthesized from cycloolefins and cyano containing ethylenic monomers are described in the U.S. Pat. No. 6,686,429, the contents of which are hereby incorporated herein by reference, may also be used.

The molecular weight of the polymers is optimized based on the type of chemistry used and on the lithographic performance desired. Typically, the weight average molecular weight is in the range of 3,000 to 30,000 and the polydispersity is in the range 1.1 to 5, preferably 1.5 to 2.5.

Other polymers of interest include those found and described in U.S. patent application Ser. No. 10/371,262, filed Feb. 21, 2003, now filed as U.S. patent application Ser. No. 10/658,840, filed Dec. 17, 2003 (and published now as US patent application publication no. 2004/0166433, the contents of which are incorporated herein by reference. Still other polymers, such as those disclosed in U.S. patent application Ser. No. 10/440,452, filed May 16, 2003 titled "Photoresist Composition for Deep UV and Process Thereof", the contents of which are hereby incorporated herein by reference, may also be used.

The solid components of the present invention are dissolved in an organic solvent. The amount of solids in the solvent or mixture of solvents ranges from about 1 weight % to about 50 weight %. The polymer may be in the range of 5 weight % to 90 weight % of the solids and the photoacid generator may be in the range of 1 weight % to about 50 weight % of the solids. Suitable solvents for such photoresists may include for example ketones such as acetone, methyl ethyl ketone, methyl isobutyl ketone, cyclohexanone, isophorone, methyl isoamyl ketone, 2-heptanone 4-hydroxy, and 4-methyl 2-pentanone; $C_1$ to $C_{10}$ aliphatic alcohols such as methanol, ethanol, and propanol; aromatic group containing-alcohols such as benzyl alcohol; cyclic carbonates such as ethylene carbonate and propylene carbonate; aliphatic or aromatic hydrocarbons (for example, hexane, toluene, xylene, etc and the like); cyclic ethers, such as dioxane and tetrahydrofuran; ethylene glycol; propylene glycol; hexylene glycol; ethylene glycol monoalkylethers such as ethylene glycol monomethylether, ethylene glycol monoethylether; ethylene glycol alkylether acetates such as methylcellosolve acetate and ethylcellosolve acetate; ethylene glycol dialkylethers such as ethylene glycol dimethylether, ethylene glycol diethylether, ethylene glycol methylethylether, diethylene glycol monoalkylethers such as diethylene glycol monomethylether, diethylene glycol monoethylether, and diethylene glycol dimethylether; propylene glycol monoalkylethers such as propylene glycol methylether, propylene glycol ethylether, propylene glycol propylether, and propylene glycol butylether; propylene glycol alkyletheracetates such as propylene glycol methylether acetate, propylene glycol ethylether acetate, propylene glycol propylether acetate, and propylene glycol butylether acetate; propylene glycol alkyletherpropionates such as propylene glycol methyletherpropionate, propylene glycol ethyletherpropionate, propylene glycol propyletherpropionate, and propylene glycol butyletherpropionate; 2-methoxyethyl ether (diglyme); solvents that have both ether and hydroxy moieties such as methoxy butanol, ethoxy butanol, methoxy propanol, and ethoxy propanol; esters such as methyl acetate, ethyl acetate, propyl acetate, and butyl acetate methyl-pyruvate, ethyl pyruvate; ethyl 2-hydroxy propionate, methyl 2-hydroxy 2-methyl propionate, ethyl 2-hydroxy 2-methyl propionate, methyl hydroxy acetate, ethyl hydroxy acetate, butyl hydroxy acetate, methyl lactate, ethyl lactate, propyl lactate, butyl lactate, methyl 3-hydroxy propionate, ethyl 3-hydroxy propionate, propyl 3-hydroxy propionate, butyl 3-hydroxy propionate, methyl 2-hydroxy 3-methyl butanoic acid, methyl methoxy acetate, ethyl methoxy acetate, propyl methoxy acetate, butyl methoxy acetate, methyl ethoxy acetate, ethyl ethoxy acetate, propyl ethoxy acetate, butyl ethoxy acetate, methyl propoxy acetate, ethyl propoxy acetate, propyl propoxy acetate, butyl propoxy acetate, methyl butoxy acetate, ethyl butoxy acetate, propyl butoxy acetate, butyl butoxy acetate, methyl 2-methoxy propionate, ethyl 2-methoxy propionate, propyl 2-methoxy propionate, butyl 2-methoxy propionate, methyl 2-ethoxypropionate, ethyl 2-ethoxypropionate, propyl 2-ethoxypropionate, butyl 2-ethoxypropionate, methyl 2-butoxypropionate, ethyl 2-butoxypropionate, propyl 2-butoxypropionate, butyl 2-butoxypropionate, methyl 3-methoxypropionate, ethyl 3-methoxypropionate, propyl 3-methoxypropionate, butyl 3-methoxypropionate, methyl 3-ethoxypropionate, ethyl 3-ethoxypropionate, propyl 3-ethoxypropionate, butyl 3-ethoxypropionate, methyl 3-propoxypropionate, ethyl 3-propoxypropionate, propyl 3-propoxypropionate, butyl 3-propoxypropionate, methyl 3-butoxypropionate, ethyl 3-butoxypropionate, propyl 3-butoxypropionate, and butyl 3-butoxypropionate; oxyisobutyric acid esters, for example, methyl-2-hydroxyisobutyrate, methyl α-methoxyisobutyrate, ethyl methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate; solvents that have both ether and hydroxy moieties such as methoxy butanol, ethoxy butanol, methoxy propanol, and ethoxy propanol; and other solvents such as dibasic esters, and gamma-butyrolactone; a ketone ether derivative such as diacetone alcohol methyl ether; a ketone alcohol derivative such as acetol or diacetone alcohol; lactones such as butyrolactone; an amide derivative such as dimethylacetamide or dimethylformamide, anisole, and mixtures thereof.

Various other additives such as colorants, non-actinic dyes, anti-striation agents, plasticizers, adhesion promoters, dissolution inhibitors, coating aids, photospeed enhancers, additional photoacid generators, and solubility enhancers (for example, certain small levels of solvents not used as part of the main solvent (examples of which include glycol ethers and glycol ether acetates, valerolactone, ketones, lactones, and the like), and surfactants may be added to the photoresist composition before the solution is coated onto a substrate. Surfactants that improve film thickness uniformity, such as fluorinated surfactants, can be added to the photoresist solution. A sensitizer that transfers energy from a particular range of wavelengths to a different exposure wavelength may also be added to the photoresist composition. Often bases are also added to the photoresist to prevent t-tops or bridging at the surface of the photoresist image. Examples of bases are amines, ammonium hydroxide, and photosensitive bases. Particularly preferred bases are trioctylamine, diethanolamine and tetrabutylammonium hydroxide.

The prepared photoresist composition solution can be applied to a substrate by any conventional method used in the photoresist art, including dipping, spraying, and spin coating. When spin coating, for example, the photoresist solution can be adjusted with respect to the percentage of solids content, in order to provide coating of the desired thickness, given the type of spinning equipment utilized and the amount of time allowed for the spinning process. Suitable substrates include silicon, aluminum, polymeric resins, silicon dioxide, doped silicon dioxide, silicon nitride, tantalum, copper, polysilicon, ceramics, aluminum/copper mixtures; gallium arsenide and other such Group III/V compounds. The photoresist may also be coated over antireflective coatings.

The photoresist coatings produced by the described procedure are particularly suitable for application to silicon/silicon dioxide wafers, such as are utilized in the production of microprocessors and other miniaturized integrated circuit components. An aluminum/aluminum oxide wafer can also be used. The substrate may also comprise various polymeric resins, especially transparent polymers such as polyesters.

The photoresist composition solution is then coated onto the substrate, and the substrate is treated (baked) at a temperature from about 70° C. to about 150° C. for from about 30 seconds to about 180 seconds on a hot plate or for from about 15 to about 90 minutes in a convection oven. This temperature treatment is selected in order to reduce the concentration of residual solvents in the photoresist, while not causing substantial thermal degradation of the solid components. In general, one desires to minimize the concentration of solvents and this first temperature. Treatment (baking) is conducted until substantially all of the solvents have evaporated and a thin coating of photoresist composition, on the order of half a micron (micrometer) in thickness, remains on the substrate. In a preferred embodiment the temperature is from about 95° C. to about 120° C. The treatment is conducted until the rate of change of solvent removal becomes relatively insignificant. The film thickness, temperature and time selection depends on the photoresist properties desired by the user, as well as the equipment used and commercially desired coating times. The coated substrate can then be imagewise exposed to actinic radiation, e.g., ultraviolet radiation, at a wavelength of from about 100 nm (nanometers) to about 300 nm, x-ray, electron beam, ion beam or laser radiation, in any desired pattern, produced by use of suitable masks, negatives, stencils, templates, etc.

The photoresist is then subjected to a post exposure second baking or heat treatment before development. The heating temperatures may range from about 90° C. to about 150° C., more preferably from about 100° C. to about 130° C. The heating may be conducted for from about 30 seconds to about 2 minutes, more preferably from about 60 seconds to about 90 seconds on a hot plate or about 30 to about 45 minutes by convection oven.

The exposed photoresist-coated substrates are developed to remove the image-wise exposed areas by immersion in a developing solution or developed by spray development process. The solution is preferably agitated, for example, by nitrogen burst agitation. The substrates are allowed to remain in the developer until all, or substantially all, of the photoresist coating has dissolved from the exposed areas. Developers include aqueous solutions of ammonium or alkali metal hydroxides. One preferred developer is an aqueous solution of tetramethyl ammonium hydroxide. After removal of the coated wafers from the developing solution, one may conduct an optional post-development heat treatment or bake to increase the coating's adhesion and chemical resistance to etching conditions and other substances. The post-development heat treatment can comprise the oven baking of the coating and substrate below the coating's softening point or UV hardening process. In industrial applications, particularly in the manufacture of microcircuitry units on silicon/silicon dioxide-type substrates, the developed substrates may be treated with a buffered, hydrofluoric acid base etching solution or dry etching. Prior to dry etching the photoresist may be treated to electron beam curing in order to increase the dry-etch resistance of the photoresist.

The invention further provides a method for producing a semiconductor device by producing a photo-image on a substrate by coating a suitable substrate with a photoresist composition. The subject process comprises coating a suitable substrate with a photoresist composition and heat treating the coated substrate until substantially all of the photoresist solvent is removed; image-wise exposing the composition and removing the image-wise exposed areas of such composition with a suitable developer.

The following examples provide illustrations of the methods of producing and utilizing the present invention. These examples are not intended, however, to limit or restrict the scope of the invention in any way and should not be construed as providing conditions, parameters or values which must be utilized exclusively in order to practice the present invention. Unless otherwise specified, all parts and percents are by weight.

EXAMPLE 1

Synthesis of bis(triphenyl sulfonium)perfluorobutane-1,4-disulfonate

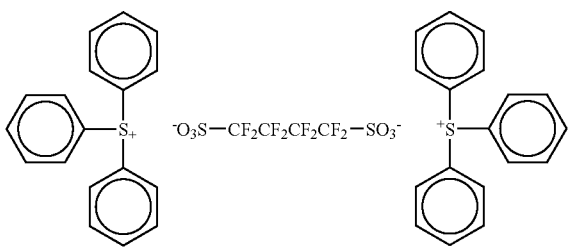

Perfluorobutane-1,4-disulfonic acid potassium salt (2.5 g) was added to a solution of triphenyl sulfonium bromide (3.5 g) in 150 ml of water. Chloroform (150 ml) was added and stirred for 5 hours. The chloroform layer was washed several times with water, dried over anhydrous sodium sulfate, filtered, and the filtrate evaporated to an oil stage. Ether was added to the oil and the mixture was stirred vigorously. A white precipitate formed. The mixture was filtered and recovered precipitate was dried under vacuum, resulting in a white powder; mp 155° C.

EXAMPLE 2

Synthesis of bis(triphenyl sulfonium)perfluoropropane-1,3-disulfonate

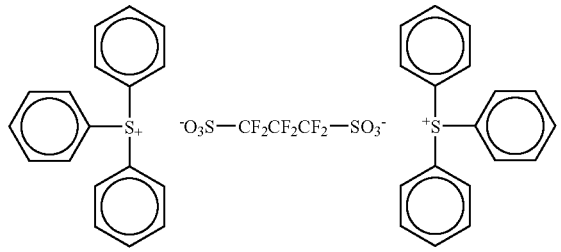

Perfluoropropane-1,3-disulfonic acid lithium salt (3.0 g) in 60 ml water was added to a solution of triphenyl sulfonium bromide (6.0 g) in 120 ml of water. Dichloromethane (200 ml) was added and stirred for 5 hours. The dichloromethane layer was washed several times with water, dried over anhydrous sodium sulfate, filtered, and the filtrate evaporated to an oil stage. Ether was added to the oil and the mixture was stirred vigorously. A white precipitate formed. The mixture was filtered and recovered precipitate was dried under vacuum, resulting in a white powder; mp 161° C.

EXAMPLE 3

Synthesis of bis(4-t-Butylphenyl iodonium) triphenyl sulfonium perfluorobutane-1,4-disulfonate

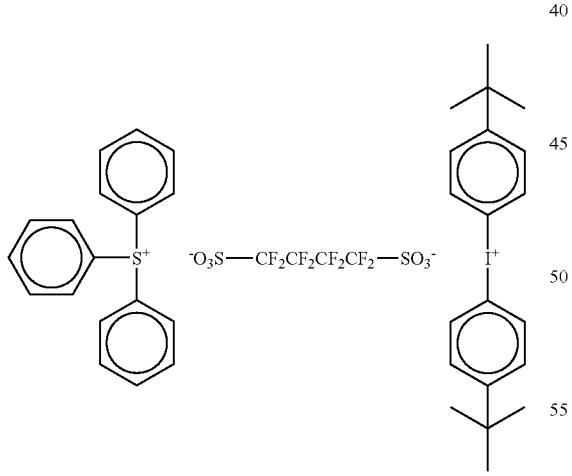

4.73 g of triphenyl sulfonium bromide was dissolved in water in a flask. Bis (4-t-butylphenyl iodonium) acetate (6.24 g) was dissolved in acetone and added to the flask. Perfluorobutane-1,4-disulfonic acid (5.0 g) was then added to the mixture and the mixture was stirred over night at room temperature. Bis (4-t-butylphenyl iodonium) triphenyl sulfonium perfluorobutane-1,4-disulfonate was isolated as in Example 1 (mixture of compounds); mp 93° C.

EXAMPLE 4

Synthesis of bis(4-t-butylphenyl iodonium) triphenyl sulfonium perfluoropropane-1,3-disulfonate

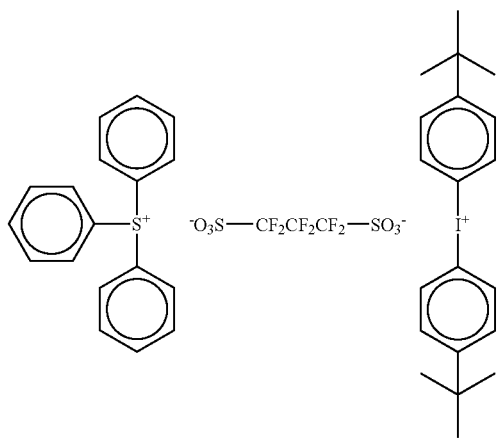

Similarly to Example 3, bis(4-t-butylphenyl iodonium) triphenyl sulfonium perfluoropropane-1,4-disulfonate can be made by using perfluoropropane-1,3-disulfonic acid instead of perfluorobutane-1,4-disulfonic acid.

EXAMPLE 5

Synthesis of bis(Benzovltetramethylenesulfonium) perfluoropropane-1,3-disulfonate

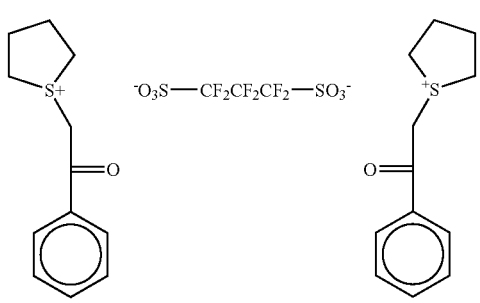

Perfluoropropane-1,3-disulfonic acid lithium salt (4.0 g) in 70 ml water was added to a solution of benzoyl tetramethylene sulfonium bromide (7.18.0 g) in 120 ml of water. The resulting mixture was stirred overnight. Dichloromethane (200 ml) was added and stirred for few hours bis(Benzoyltetramethylenesulfonium)perfluoropropane-1,3-disulfonate was isolated as in example 2, mp 192° C.

EXAMPLE 6

Synthesis of bis(Benzoyltetramethylenesulfonium) perfluorobutane-1,4-disulfonate

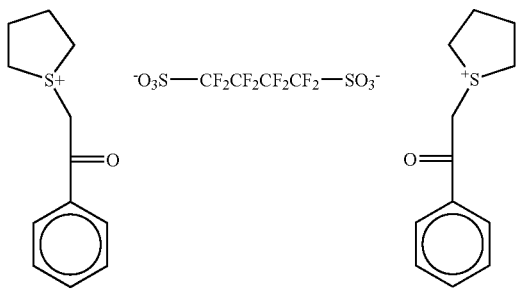

Similarly to Example 5, bis(Benzoyltetramethylenesulfonium)perfluorobutane-1,3-disulfonate can be made by using perfluorobutane-1,4-disulfonic acid lithium salt instead of perfluoropropane-1,3-disulfonic acid lithium salt.

EXAMPLE 7A

Synthesis of bis(tris(4-t-butyl phenyl)sulfonium)perfluorobutane-1,4-disulfonate

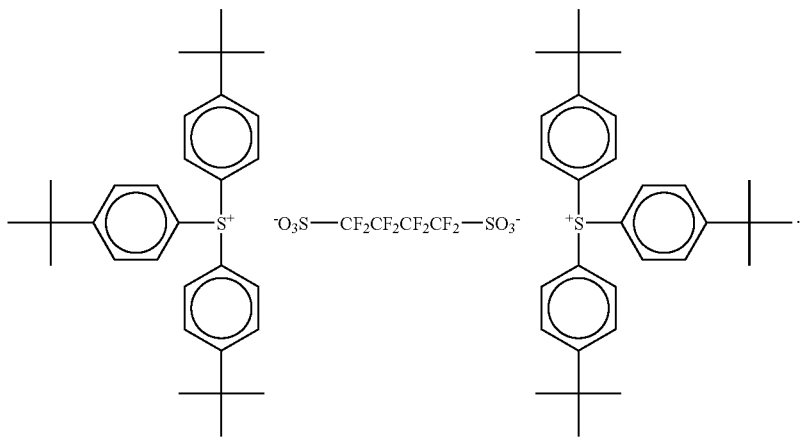

Perfluorobutane-1,4-disulfonic acid potassium salt (2.92 g) in 100 ml water was added to a solution of tris(4-t-butyl phenyl) sulfonium hydroxide (7.75 g) in 150 ml of acetone. Chloroform (150 ml) was added and stirred for 5 hours. The chloroform layer was washed several times with water, dried over anhydrous sodium sulfate, filtered, and the filtrate evaporated to an oil stage. Ether was added to the oil and the mixture was stirred vigorously. A white precipitate formed. The mixture was filtered and the recovered precipitate was dried under vacuum, resulting in a white powder; mp 190° C.

EXAMPLE 7B

Alternate Synthesis of bis(tris(4-t-butyl phenyl)sulfonium)perfluorobutane-1,4-disulfonate Perfluorobutane-1,4-disulfonic acid potassium salt (0.1887 g) in 2 ml water was added to a solution of tris(4-t-butyl phenyl) sulfonium triflate (0.5000 g) in 1.14 g methanol and stirred for 1 hour. This solution was then extracted with chloroform (7 mL). The chloroform layer was washed several times with distilled water and stripped of solvent, and the residue dried under high vacuum. This oil was then recrystallized two times from a mixture of diethyl ether and methylene chloride and the crystals dried at 45° C. overnight under vacuum to give after drying 0.34 g of material.

EXAMPLE 8A

Synthesis of bis(tris(4-t-butyl phenyl)sulfonium)perfluoropropane-1,3-disulfonate

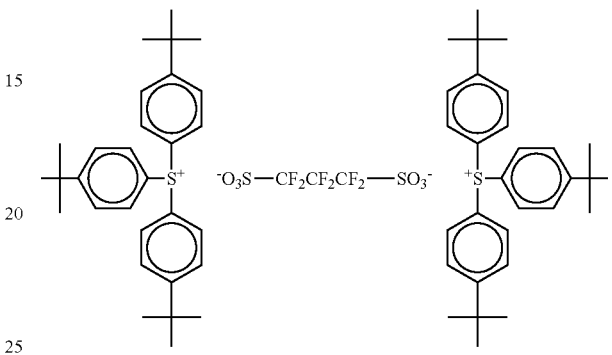

This material can be synthesized by using the procedure in Example 7, using perfluoropropane-1,3-disulfonic acid potassium salt in place of perfluorobutane-1,4-disulfonic acid potassium salt.

EXAMPLE 8B

Alternate Synthesis of bis(tris(4-t-butyl phenyl)sulfonium)perfluoropropane-1,3-disulfonate Perfluoropropane-1,3-disulfonic lithium salt (0.1390 g) in 1 ml water was added to a solution of tris(4-t-butyl phenyl) sulfonium triflate (0.5000 g) in 1 mL methanol and stirred for 1 hour. This solution was then extracted with chloroform (7 mL). The chloroform layer was washed several times with distilled water and stripped of solvent, and the residue dried under high vacuum. This oil was then recrystallized two times from a mixture of diethyl ether and methylene chloride and the crystals dried at 45° C. overnight under vacuum to give after drying 0.30 of material.

EXAMPLE 9

Synthesis of bis(4-t-butylphenyl diphenyl sulfonium)perfluorobutane-1,4-disulfonate

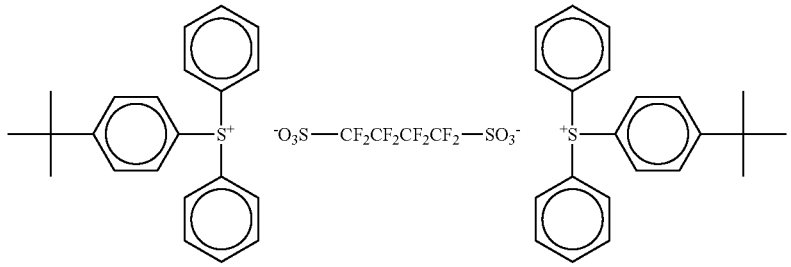

This material was made following Example 1 except perfluorobutane-1,4-disulfonic acid potassium salt and bis(4-t-butylphenyl diphenylsulfonium) bromide were used.

EXAMPLE 10

Synthesis of bis(4-t-butylphenyl diphenyl sulfonium)perfluoropropane-1,3-disulfonate

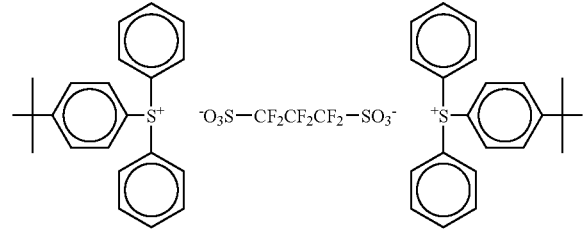

This material was made following the procedure in Example 9 except that perfluoropropane-1,3-disulfonic acid potassium salt was used instead of perfluoropropane-1,4-disulfonic acid potassium salt.

EXAMPLE 11

Synthesis of bis(triphenyl sulfonium)perfluoropropane-1-carboxylate-3-sulfonate

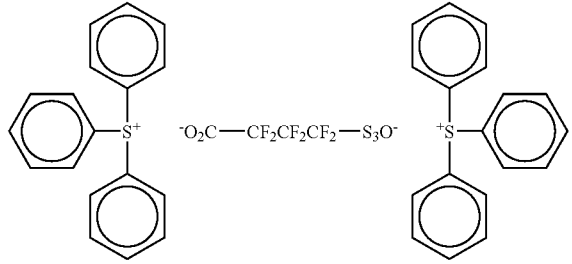

This material was made following the procedure in Example 1 except that perfluoropropane-1-carboxylic acid-3-sulfonic acid lithium salt was used instead of perfluorobutane-1,4-disulfonic acid potassium salt.

EXAMPLE 12

Synthesis of bis(triphenyl sulfonium)perfluorobutane-1-carboxylate-4-sulfonate

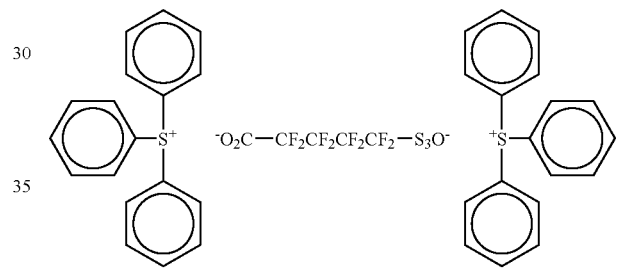

This material can be made following the procedure in Example 1 except that perfluorobutane-1-carboxylic acid-4-sulfonic acid lithium salt is used instead of perfluorobutane-1,4-disulfonic acid.

EXAMPLE 13

Synthesis of bis(4-t-butylphenyl iodonium)triphenyl sulfonium Perfluoropropane-1-carboxylate-3-sulfonate

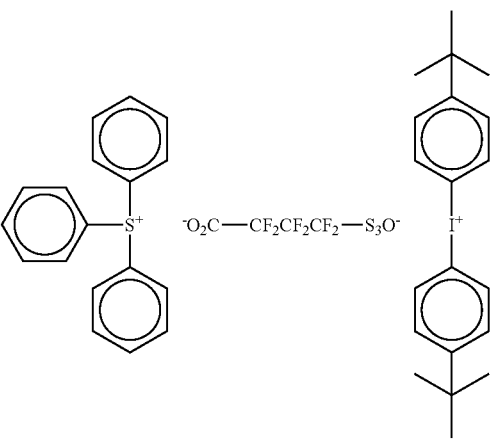

This material can be made following the procedure in Example 3 except that perfluoropropane-1-carboxylic acid-3-sulfonic acid lithium salt is used instead of perfluorobutane-1,4-disulfonic acid.

EXAMPLE 14

Synthesis of bis(4-t-butylphenyl iodonium)triphenyl sulfonium perfluorobutane-1-carboxylate-4-sulfonate

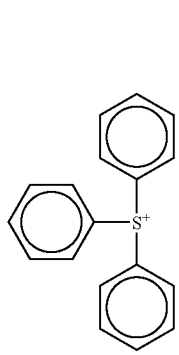 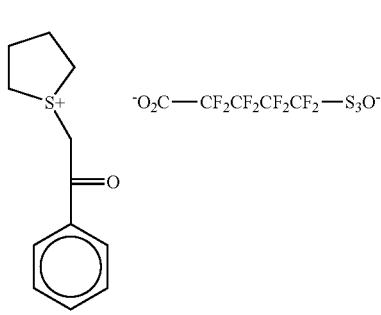

This material can be made following the procedure in Example 3 except that perfluorobutane-1-carboxylic acid-4-sulfonic acid lithium salt is used instead of perfluorobutane-1,4-disulfonic acid.

EXAMPLE 15

Synthesis of bis(Benzoyltetramethylenesulfonium) perfluoropronane-1-carboxylate-3-sulfonate

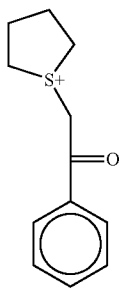 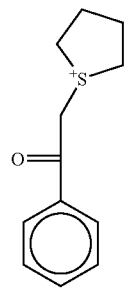

This material can be made following the procedure in Example 5 except that perfluoropropane-1-carboxylic acid-3-sulfonic acid lithium salt is used instead of perfluoropropane-1,3-disulfonic acid lithium salt.

EXAMPLE 16

Synthesis of bis(Benzovltetramethylenesulfonium) perfluorobutane-1-carboxylate-4-sulfonate

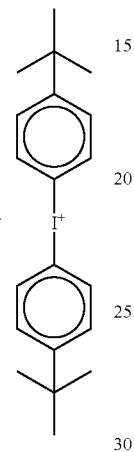

This material can be made following the procedure in Example 5 except that perfluorobutane-1-carboxylic acid-4-sulfonic acid lithium salt is used instead of perfluoropropane-1,3-disulfonic acid lithium salt.

EXAMPLE 17

Synthesis of bis(tris(4-t-butyl phenyl)sulfonium) perfluoropropane-1-carboxylate-3-sulfonate

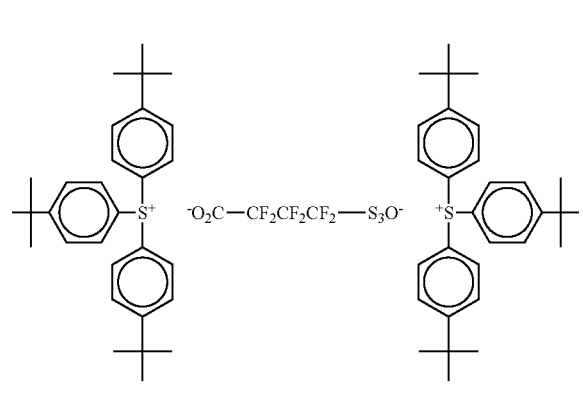

This material can be made following the procedure in Example 7 except that perfluoropropane-1-carboxylic acid-3-sulfonic acid lithium salt is used instead of perfluorobutane-1,4-disulfonic acid potassium salt.

EXAMPLE 18

Synthesis of bis(tris(4-t-butyl phenyl)sulfonium) perfluorobutane-1-carboxylate-4-sulfonate

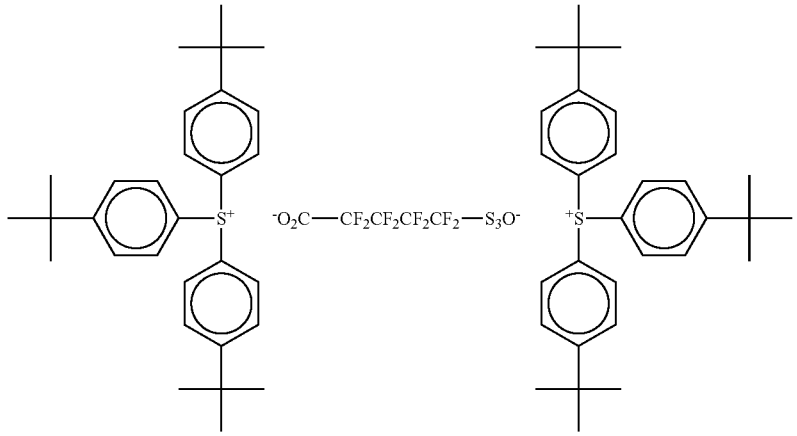

This material can be made following the procedure in Example 7 except that perfluorobutane-1-carboxylic acid-4-sulfonic acid lithium salt is used instead of perfluorobutane-1,4-disulfonic acid potassium salt.

EXAMPLE 19

Synthesis of bis(4-t-butylphenyl diphenyl sulfonium) perfluoropropane-1-carboxylate-3-sulfonate

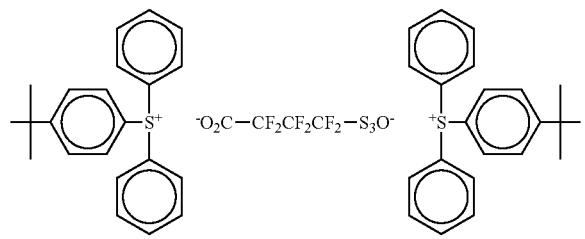

This material can be made following Example 1 except perfluoropropane-1-carboxylic acid-3-sulfonic acid lithium salt and bis(4-t-butylphenyl diphenylsulfonium)bromide are used.

EXAMPLE 20

Synthesis of bis(4-t-butylphenyl diphenyl sulfonium) perfluorobutane-1-carboxylate-4-sulfonate

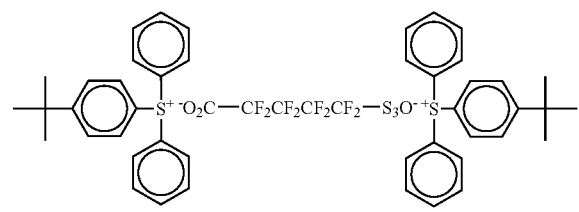

This material can be made following Example 1 except perfluorobutane-1-carboxylic acid-4-sulfonic acid lithium salt and bis(4-t-butylphenyl diphenylsulfonium)bromide are used.

EXAMPLE 21A

Synthesis of bis(4-t-butylphenyl)iodonium chloride

To a 2 L three necked flask (equipped with a mechanical stirrer, thermometer, addition funnel, and condenser/nitrogen inlet) was added potassium iodate (100 g) methylene chloride (240 mL), acetic anhydride (200 mL) and tert-butylbenzene (254 mL). This stirred reaction mixture was cooled to 5° C. and concentrated sulfuric acid (100 mL) was added slowly using the dropping funnel so as to maintain the temperature between 5 and 10° C. After the addition was complete the reaction mixture was maintained at 5° C. and stirred for 5 hours. After this time the reaction mixture was quenched by the slow addition of 100 mL of distilled water while stirring and maintaining the temperature between 5 and 10° C. The reaction mixture was poured into a separatory funnel, and the methylene chloride layer was removed and washed three times with 100 mL aliquots of distilled water. The washed methylene chloride layer was stripped of solvents on a rotoevaporator and further dried by high vacuum (1 mm Hg) to remove most of the remaining tert-butylbenzene. The resultant residue was dissolved into 200 mL of methylene chloride and to this was added 27.3 grams of sodium chloride. This mixture was stirred with a magnetic stirrer at 1000 rpm overnight. After stirring, the mixture was placed in a separatory funnel, the methylene chloride layer removed and washed four times with 100 mL aliquots of distilled water. The washed organic layer was stripped of solvent and dried under high vacuum to remove any remaining tert-butylbenzene. The residue was triturated with 4 times with 200 mL aliquots of hexane and precipitated with ether (500 mL) to give 86 grams of crude material after drying. This crude material was dissolved in 170 mL of methylene chloride and recrystallized by the addition of 500 mL of diethyl ether to promote crystallization. These crystals were filtered, dried to give 77 grams of product.

EXAMPLE 21B

Synthesis of Silver Methane Disulfonate

A 50% solution of methanedisulfonic acid in water (2.5 grams) was diluted in 25 mL of water into which, while stirring, silver carbonate (3.91 grams) was added slowly. The silver carbonate dissolved with effervescence of carbon dioxide. After the reaction was complete remaining insoluble material was removed by filtration and the filtrate was stripped of water and dried under high vacuum at 45° C. to give 4.9 grams of white crystals.

EXAMPLE 21C

Synthesis of bis(4-t-butylphenyl iodonium)methane disulfonate

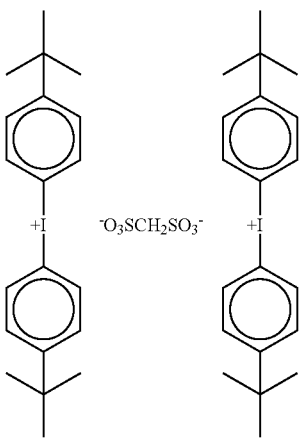

Five grams ($1.16609 \times 10^{-2}$ mol) of bis(4-t-butylphenyl) iodonium chloride from Example 21A was suspended in 40 ml of acetonitrile with stirring. 2.27 grams ($5.8304 \times 10^{-3}$ mol) of silver methane disulfonate from Example 21B was then added together with 5 ml of water. The solution was stirred overnight.

The solution was then filtered and the filtrate was recovered. The filtrate was then filtered through a 0.2 μm PTFE filter (using a syringe) to remove any colloidal silver chloride. The filtrate was recovered and placed in a rotovap to remove solvent.

The remaining residue was then recrystallized using methylene chloride (hot) and ether. This was repeated twice. The remaining material (solid) was then washed using water and methylene chloride. The organic phase was retained and the solvent removed by drying under vacuum, yielding 4 grams of bis(4-t-butylphenyl iodonium) methane disulfonate.

EXAMPLE 22

Synthesis of bis(triphenyl sulfonium)methane disulfonate

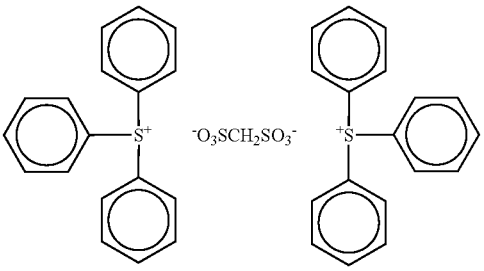

0.979533 grams (0.002853 mol) of triphenyl sulfonium bromide were placed into 40 ml of acetonitrile and then 0.556263 grams (0.001427 mol) of silver methane disulfonate and 1 ml of water were added with stirring. The solution was stirred overnight and recrystallized as in Example 21.

EXAMPLE 23

Synthesis of bis(44-butylphenyl iodonium)perfluoromethane disulfonate

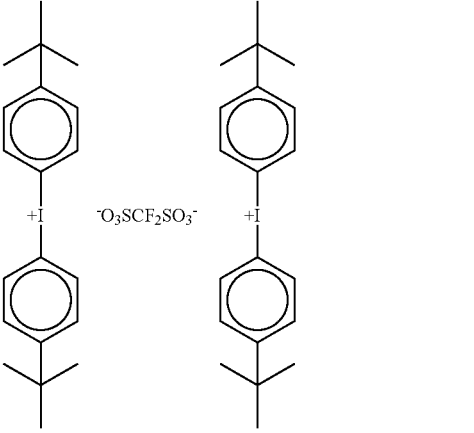

This material can be made following Example 21 except silver perfluoromethane disulfonate is used in place of silver methane disulfonate.

EXAMPLE 24

Synthesis of bis(triphenyl sulfonium)perfluoromethane disulfonate

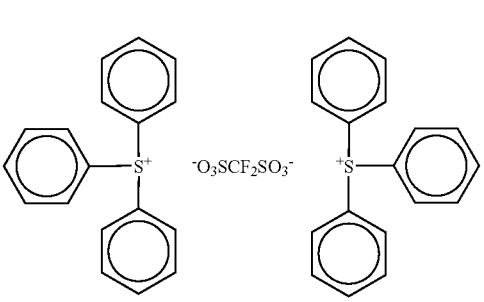

This material can be made following Example 22 except silver perfluoromethane disulfonate is used in place of silver methane disulfonate.

EXAMPLE 25

Synthesis of bis(4-t-butylphenyl iodonium)triphenyl sulfonium perfluoromethane disulfonate

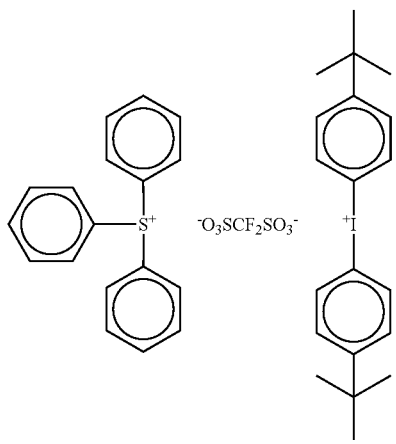

This material can be made following the procedure in Example 23 except that equal molar amounts of bis(4t-butylphenyl) iodonium chloride and triphenylsulfonium bromide are used.

EXAMPLE 26

Synthesis of bis(4-t-butylphenyl iodonium)triphenyl sulfonium methane disulfonate

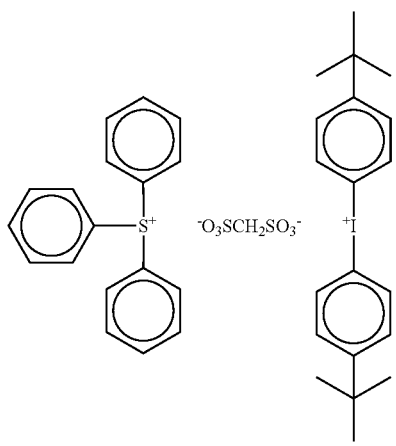

This material can be made following the procedure in Example 25 except that silver methane disulfonate is used instead of silver perfluoromethane disulfonate.

EXAMPLE 27

Synthesis of bis(Benzoyltetramethylenesulfonium) perfluoromethane disulfonate

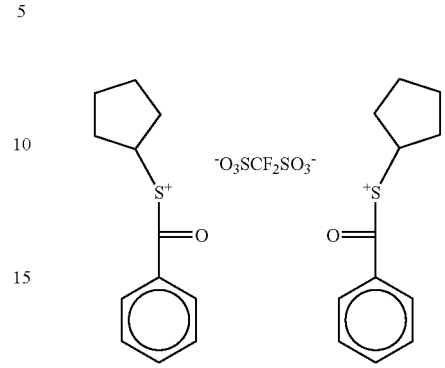

This material can be made by following the procedure in Example 23 except that benzoyl tetramethylene sulfonium bromide is used in place of triphenyl sulfonium bromide.

EXAMPLE 28

Synthesis of bis(Benzovltetramethylenesulfonium)methane disulfonate

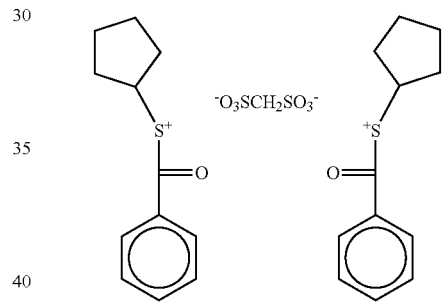

This material can be made by following the procedure in Example 27 except that silver methane disulfonate is used in place of silver perfluoromethane disulfonate.

EXAMPLE 29

Synthesis of bis(tris(4-t-butyl phenyl)sulfonium)perfluoromethane disulfonate

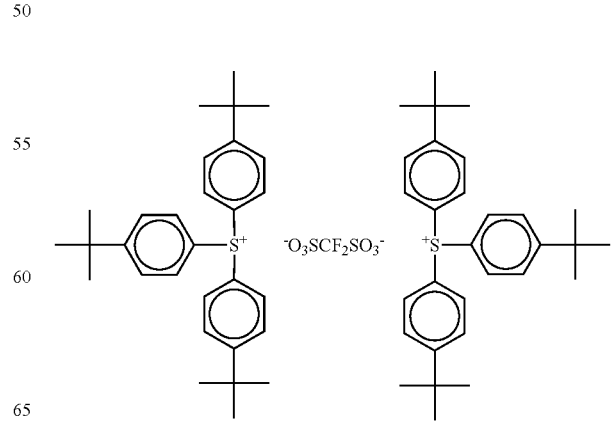

This material can be made by following the procedure in Example 23 except that tris(4-t-butyl phenyl) sulfonium chloride is used instead of bis(4-t-butylphenyl) iodonium chloride.

EXAMPLE 30

Synthesis of bis(tris(4-t-butyl phenyl)sulfonium)methane disulfonate

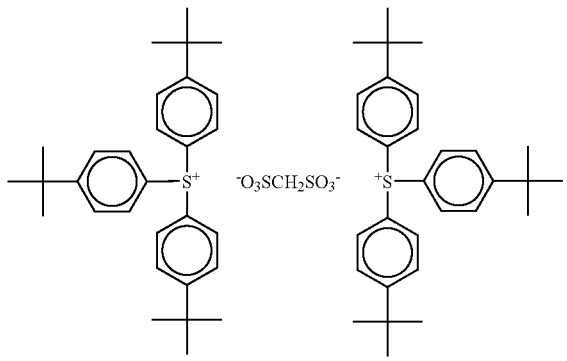

This material can be made by following the procedure in Example 29 except that silver methane disulfonate is used in place of silver perfluoromethane disulfonate.

EXAMPLE 31

Synthesis of bis(4-t-butylphenyl diphenylsulfonium)perfluoromethane disulfonate

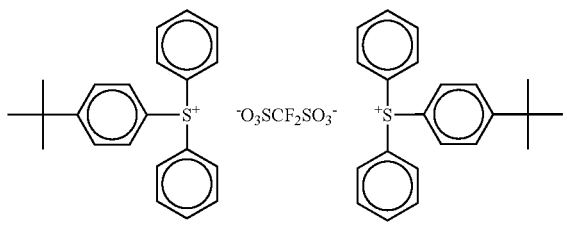

This material can be made by following the procedure in Example 29 except that (4-t-butylphenyl diphenylsulfonium) chloride is used instead of tris(4-t-butyl phenyl)sulfonium chloride.

EXAMPLE 32

Synthesis of bis(44-butylphenyl diphenylsulfonium)methane disulfonate

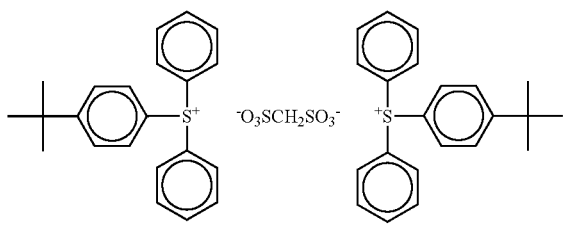

This material can be made by following the procedure in Example 31 except that silver methane disulfonate is used instead of silver perfluoromethane disulfonate.

EXAMPLE 33

Synthesis of bis(4-octyloxyphenyl iodonium)perfluorobutane-1,4-disulfonate

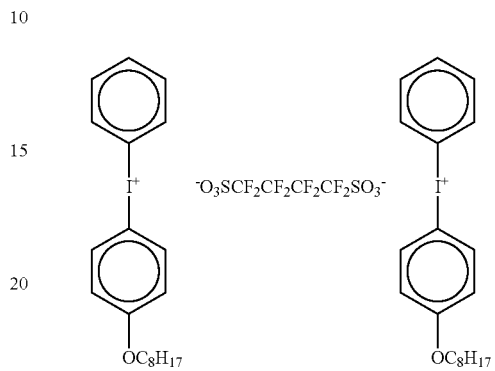

Bis(4-t-octyloxyphenyl)iodonium hexafluoroantimonate (available from Hampford Research Inc, 54, Veterans Boulivard, Stanford, Conn. 06615)) was dissolved in acetone to make a 10% solution. Approximately 65.8 of this 10% solution and 40 ml of acetone were then passed through an ion exchange column which contained A-21 ion exchange resin (bed volume 100 ml) two times. Approximately 3.8 g of perfluorobutane-1,4-disulfonic acid potassium salt was dissolved in 100 ml of deionized water. This solution and the solution that was passed through the ion exchange resin were mixed with stirring in a beaker for 1 hour. Dichloromethane was then added to the beaker with stirring and allowed to stir overnight. Thereafter, deionized water was added to the beaker and the organic layer was separated using a separatory funnel. The organic layer was washed several times with water and then the organic solvent was evaporated, leaving an oil.

EXAMPLE 33A

The following compounds can be made following the procedures outlined herein:
bis(4-octyloxyphenyl iodonium)ethane disulfonate
bis(4-octyloxyphenyl iodonium)perfluoroethane disulfonate
bis(4-octyloxyphenyl iodonium)perfluoropropane-1,3-disulfonate
bis(4-octyloxyphenyl iodonium)perfluoropropane-1-carboxylate-3-sulfonate
bis(4-octyloxyphenyl iodonium)perfluorobutane-1-carboxylate-4-sulfonate
bis(4-octyloxyphenyl iodonium)methane disulfonate
bis(4-octyloxyphenyl iodonium)perfluoromethane disulfonate

EXAMPLE 34A

Synthesis of bis(4-octyloxyphenyl)phenyl sulfonium triflate 20 g (0.05893 mol) of bis(sodium oxyphenyl)phenyl sulfonium triflate was placed into a round bottom flask and 80 g of anhydrous DMSO was added to the flask with stirring to form a suspension. 30 g (0.1297 mol; 10% excess) of octyl bromide was added and the mixture was allowed to react for 3 days. The mixture was filtered and the filtrate was added to 600 ml of deionized water. The aqueous layer was extracted with 200 mL of $CH_2CL_2$. The $CH_2CL_2$ layer was retained and washed with three 100 mL aliquots of distilled water and the solvent stripped off with a rotoevaporator and further dried under high vacuum to remove as much as possible any remaining octyl bromide. The residue from this was triturated with four 50 mL aliquots of pentane. This residue consisted of almost pure bis (octyloxyphenyl)phenyl sulfonium triflate with a small amount of bromide contamination (21.99 grams). If desired, this product can be purified by dissolving the crude product in 30 mL of methanol to which is added 6.2 grams of potassium triflate dissolved in 30 mL of water. After stirring for half and hour the reaction mixture was stripped of solvent and the residue suspended in $CH_2CL_2$ (50 mL) and extracted with water (20 mL) five times. The final washed organic layer was stripped of solvents as above, and triturated with pentane as above. The final triturated product was dried under high vacuum overnight (16.35 grams) and the remaining oil was dissolved in THF (~20 ml). 100 ml of deionized water was then added to the mixture and stirred. The aqueous layer was decanted. An additional 10 ml of THF and 100 ml of deionized water was added to the mixture and allowed to stand in a refrigerator overnight. The aqueous layer was then decanted and the remaining organic solvent was removed using a Rotovap with high vacuum. The residue was extracted twice using chloroform and deionized water rinses. Finally, the remaining material was extracted three times using pentane and dried overnight under vacuum.

EXAMPLE 34B

Synthesis of bis(4-octyloxyphenyl)phenyl sulfonium perfluorobutane-1,4-disulfonate

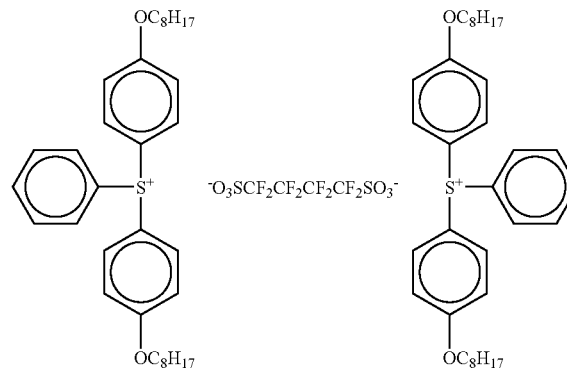

The compound of Example 34A (15 grams) was dissolved in 15 mL of methanol. To this was added 10.5 grams of dipotassium 1,4-perfluorobutane disulfonate dissolved in a hot mixture of methanol and water (90/80 methanol/water) while heating the whole solution to boiling so as to maintain a clear one-phase solution with no precipitate. This solution was allowed to cool while stirring and stirred overnight at room temperature. This solution was stripped of solvents on a roto-evaporator and then suspended in 100 mL of methylene chloride and washed with three times with 40 mL of distilled water. This procedure was repeated 6 times to give material which was pure 1,4-perfluorobutanedisulfonate (13.42 grams)

EXAMPLE 34C

The following compounds can be made following the procedures in Examples 34A and 34B by using instead of potassium 1,4-perfluorobutane disulfonate an equimolar amount of the corresponding disulfonate salt or disulfonic acid:
bis(4-octyloxyphenyl)phenyl sulfonium ethane disulfonate
bis(4-octyloxyphenyl)phenyl sulfonium perfluoroethane disulfonate
bis(4-octyloxyphenyl)phenyl sulfonium perfluoropropane-1,3-disulfonate
bis(4-octyloxyphenyl)phenyl sulfonium perfluoropropane-1-carboxylate-3-sulfonate
bis(4-octyloxyphenyl)phenyl sulfonium perfluorobutane-1-carboxylate-4-sulfonate
bis(4-octyloxyphenyl)phenyl sulfonium methane disulfonate
bis(4-octyloxyphenyl)phenyl sulfonium perfluoromethane disulfonate

EXAMPLE 35

Synthesis of Synthesis of bis[bis[4-pentafluorobenzenesulfonyloxyphenyl]phenylsulfonium]perfluorobutane-1,4-disulfonate

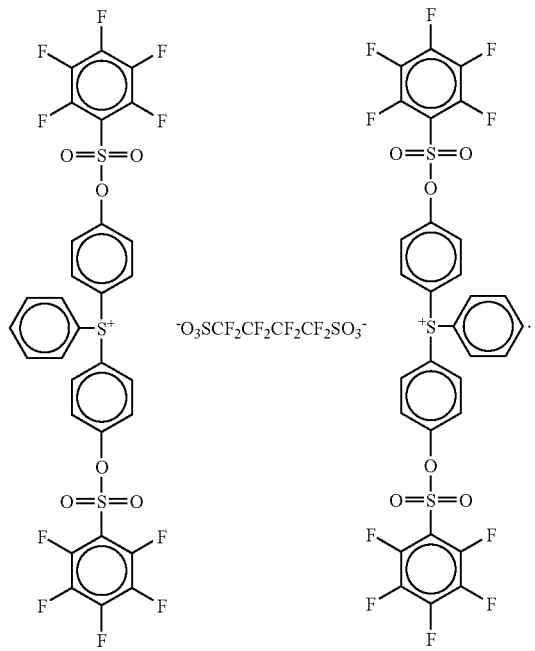

Bis[4-hydroxylphenyl]phenysulfonium perfluoromethanesulfonate (37.60 g) and an acetone-water mixture were placed into a reaction vessel equipped with an agitator, a thermometer, a reflux condenser, and a tube for introducing nitrogen gas into the vessel. Under a nitrogen blanket, 18.54 g perfluorobutane-1,4-disulfonic acid potassium salt was added to the reaction vessel and the mixture was stirred overnight. Dichloromethane (150 ml) and water were added to the reaction vessel and the mixture was stirred for 2 hours. The mixture was then placed into a separatory funnel and the organic (dichloromethane) layer was retained. The dichloromethane layer was washed with water (300 ml×3). The dichloromethane was evaporated under vacuum and ether was added to remaining material with stirring. A white precipitate formed, was filtered from the mixture, and dried in a vacuum oven (yield 35 g; mp 195° C.).

Bis[bis[4-hydroxylphenyl]phenysulfonium]perfluorobutane-1,4-disulfonate (3.5 g) from above and dry THF where placed into a reaction vessel equipped with an agitator, a thermometer, reflux condenser, and a tube for introducing nitrogen gas into the vessel. A dry ice-acetone bath was placed around the vessel. 5.0 g of pentafluorobenzene sulfonyl chloride was added to the vessel and the mixture was stirred for 5 hours. Dichloromethane (150 ml) and water were added to the vessel and the mixture was stirred for an additional 2 hours. The mixture was placed into a separatory funnel and the dichloromethane layer was retained. The dichloromethane layer was washed several times with water, dried over anhydrous sodium sulfate, filtered, and the remaining volatile materials were evaporated to leave an oil. Ether was added to the oil and the mixture was stirred vigorously. White crystals of bis[bis[4-pentafluorobenzenesulfonyloxyphenyl]phenysulfonium]perfluorobutane-1,4-disulfonate were formed (mp 61-63° C.).

EXAMPLE 35A

The following compounds can be made following the procedures herein:
bis[bis[4-pentafluorobenzenesulfonyloxyphenyl]phenylsulfonium]ethane disulfonate
bis[bis[4-pentafluorobenzenesulfonyloxyphenyl]phenylsulfonium]perfluoroethane disulfonate
bis[bis[4-pentafluorobenzenesulfonyloxyphenyl]phenylsulfonium]perfluoropropane-1,3-disulfonate
bis[bis[4-pentafluorobenzenesulfonyloxyphenyl]phenylsulfonium]perfluoropropane-1-carboxylate-3-sulfonate
bis[bis[4-pentafluorobenzenesulfonyloxyphenyl]phenylsulfonium]perfluorobutane-1-carboxylate-4-sulfonate
bis[bis[4-pentafluorobenzenesulfonyloxyphenyl]phenylsulfonium]methane disulfonate
bis[bis[4-pentafluorobenzenesulfonyloxyphenyl]phenylsulfonium]perfluoromethane disulfonate

EXAMPLE 36

Synthesis of bis[bis[4-(3,5-di(trifluoromethyl)benzenesulfonyloxy)-phenyl]phenylsulfonium]perfluorobutane-1,4-disulfonate

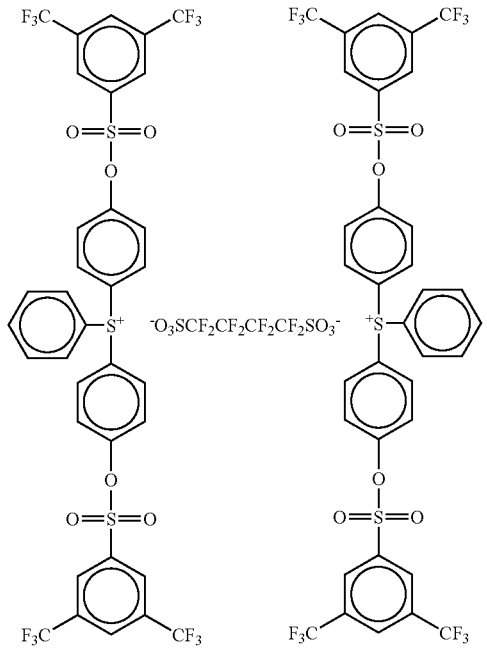

This can be made by using 3,5-di(trifluoromethyl)benzene sulfonyl chloride instead of pentafluorobenzene sulfonyl chloride and following the procedure in Example 35.

EXAMPLE 36A

The following compounds can be made following the procedures herein:
bis[bis[4-(3,5-di(trifluoromethyl)benzenesulfonyloxy)phenyl]phenylsulfonium]ethane disulfonate
bis[bis[4-(3,5-di(trifluoromethyl)benzenesulfonyloxy)phenyl]phenylsulfonium]perfluoroethane disulfonate
bis[bis[4-(3,5-di(trifluoromethyl)benzenesulfonyloxy)phenyl]phenylsulfonium]perfluoropropane-1,3-disulfonate
bis[bis[4-(3,5-di(trifluoromethyl)benzenesulfonyloxy)phenyl]phenylsulfonium]perfluoropropane-1-carboxylate-3-sulfonate
bis[bis[4-(3,5-di(trifluoromethyl)benzenesulfonyloxy)phenyl]phenylsulfonium]perfluorobutane-1-carboxylate-4-sulfonate
bis[bis[4-(3,5-di(trifluoromethyl)benzenesulfonyloxy)phenyl]phenylsulfonium]methane disulfonate Other examples of compounds related to the invention include Bis(4-t-butylphenyl iodonium)ethane disulfonate, bis(4-t-butylphenyl iodonium)perfluoroethane disulfonate, bis(triphenyl sulfonium)ethane disulfonate, bis(triphenyl sulfonium)perfluoroethane disulfonate, bis(4-t-butylphenyl iodonium)triphenyl sulfonium perfluoroethane disulfonate, bis(4-t-butylphenyl iodonium)triphenyl sulfonium ethane disulfonate, bis(benzoyltetramethylenesulfonium)perfluoroethane disulfonate, bis(benzoyltetramethylenesulfonium) ethane disulfonate, bis(tris(4-t-butyl phenyl)sulfonium)perfluoroethane disulfonate, bis(tris(4-t-butyl phenyl) sulfonium)ethane disulfonate, bis(4-t-butylphenyl diphenylsulfonium)perfluoroethane disulfonate, bis(4-t-butylphenyl diphenylsulfonium)ethane disulfonate, which can be made by using silver ethane disulfonate or silver perfluoroethane disulfonate as in the above Examples. Other representative examples of compounds of the present invention include bis[bis[2-methyladamantylacetyloxymethoxyphenyl]phenylsulfonium]perfluorobutane-1,4-disulfonate, bis[bis[2-methyladamantylacetyl-oxymethoxyphenyl]phenylsulfonium]ethane disulfonate, bis[bis[2-methyl-adamantylacetyloxymethoxyphenyl] phenylsulfonium]perfluoroethane disulfonate, bis[bis[2-methyladamantylacetyloxymethoxyphenyl] phenylsulfonium]perfluoro-propane-1,3-disulfonate, bis[bis[2-methyladamantylacetyloxymethoxyphenyl] phenylsulfonium]perfluoropropane-1-carboxylate-3-sulfonate, bis[bis[2-methyladamantylacetyloxymethoxyphenyl]phenylsulfonium] perfluorobutane-1-carboxylate-4-sulfonate, bis[bis[2-methyladamantylacetyloxymethoxyphenyl] phenylsulfonium]methane disulfonate, and bis[bis[2-methyladamantyl-acetyloxymethoxyphenyl] phenylsulfonium]perfluoromethane disulfonate, where the cation portion can be made from bis[4-hydroxylphenyl] phenysulfonium bromide and 2-methyladamantylbromoacetate and the resulting cation is then reacted with the respective anion lithium (or potassium) salt. Additional representative examples of compounds of the present invention include bis[bis[4,4-bis(trifluoromethyl)-3-oxatricyclo [4.2.1.0$^{2,5}$]-nonylmethoxyphenyl]phenyl sulfonium]perfluorobutane-1,4-disulfonate, bis[bis[4,4-bis(trifluoromethyl)-3-oxatricyclo[4.2.1.0$^{2,5}$]-nonylmethoxy-phenyl]phenyl sulfonium]ethane disulfonate, bis[bis[4,4-bis(trifluoromethyl)-3-oxatricyclo[4.2.1.0$^{2,5}$]-nonylmethoxyphenyl]phenyl sulfonium]perfluoroethane disulfonate, bis[bis[4,4-bis(trifluoromethyl)-3-oxatricyclo[4.2.1.0$^{2,5}$]-nonylmethoxyphenyl]phenyl sulfonium]perfluoropropane-1,3-disulfonate, bis[bis[4,4-bis(trifluoro-methyl)-3-oxatricyclo[4.2.1.0$^{2.5}$]-nonylmethoxyphenyl]phenyl sulfonium]-perfluoropropane-1-carboxylate-3-sulfonate, bis[bis[4,4-bis(trifluoromethyl)-3-oxatricyclo[4.2.1.0$^{25}$]-nonylmethoxyphenyl]phenyl sulfonium]perfluorobutane-1-carboxylate-4-sulfonate, bis[bis[4,4-bis(trifluoromethyl)-3-oxatricyclo[4.2.1.0$^{2,5}$]-nonylmethoxyphenyl]phenyl sulfonium]methane disulfonate, and bis[bis[4,4-bis(trifluoromethyl)-3-oxatricyclo[4.2.1.0$^{2,5}$]-nonylmethoxyphenyl]phenyl sulfonium]-perfluoromethane disulfonate here the cation portion can be made from bis[4,4-bis(trifluoromethyl)-3-oxatricyclo[4.2.1.0$^{2.5}$]-nonylmethoxyphenyl]phenyl sulfonium bromide and 4,4-bis(trifluoromethyl)-3-oxatricyclo[4.2.1.0$^{2,5}$]nonyl chloromethylether and the resulting cation is then reacted with the respective anion lithium (or potassium) salt.

EXAMPLE 37

1.073 g of poly(MAdMA/HAdA/ANBL; 50/20/30) polymer, 0.0476 g (50 µmol/g) of bis(triphenyl sulfonium)perfluorobutane-1,4-disulfonate from Example 1, 0.43 g of DIPA (1 weight % in propylene glycol monomethyl ether acetate (PGMEA)) and 0.03 g of 10 weight % PGMEA solution of a surfactant (fluoroaliphatic polymeric ester, supplied by 3M Corporation, St. Paul Minn.) were dissolved in 23.872 of AZ Thinner (propylene glycol monomethyl ether acetate/propylene glycol monomethyl ether) to form a photoresist solution.

EXAMPLE 38

A silicon substrate coated with a bottom antireflective coating (B.A.R.C.) was prepared by spin coating the bottom antireflective coating solution (AZ® EXP ArF-1, B.A.R.C. available from AZ Electronic Materials USA Corp., Somerville, N.J.) onto the silicon substrate and baking at 215° C. for 60 sec. The B.A.R.C film thickness was 29 nm. The photoresist solution from Example 37 was then coated on the B.A.R.C coated silicon substrate. The spin speed was adjusted such that the photoresist film thickness was thickness 180 nm. The photoresist was then exposed (Nikon 306D 0.85NA & 415 Annular Illumination, PAB100° C./60 s, PEB 110° C./60 s, Development time: 30 s (ACT12), 6% PSM). The imaged photoresist was then developed using a 2.38 weight % aqueous solution of tetramethyl ammonium hydroxide for 30 sec. The line and space patterns were then observed on a scanning electron microscope. The photoresist had a photosensitivity of 47.6 mJ/cm$^2$ and had very good exposure latitude (16.8%), good LER and profile shape.

EXAMPLE 39

0.64 g of poly(EAdMA/HAdA/α-GBLMA/α-GBLA; 30/30/20/20) polymer, 0.0170 g (30 µmol/g) of bis triphenyl sulfonium perfluorobutane-1,4-disulfonate from Example 1, and 0.0198 g of t-butyldiphenyl iodonium bis-perfluoroethane sulfonimide from 3M Corporation, 0.2781 g of DIPA 1 weight % in methyl-2-hydroxyisobutyrate (MHIB)) and 0.0204 g of 10 weight % PGMEA solution of a surfactant (fluoroaliphatic polymeric ester, supplied by 3M Corporation, St. Paul Minn.) were dissolved in 12.58 of MHIB) to form a photoresist solution.

EXAMPLE 40

Example 38 was repeated with the photoresist from Example 39 and good results were obtained.

EXAMPLE 41

1.095 g of poly(EAdMA/HAdA/α-GBLMA/AdMA; 30/20/40/10) polymer, 0.0282 g (30 µmol/g) of bis triphenyl sulfonium perfluorobutane-1,4-disulfonate from Example 1, and 0.0328 g of bis(4-t-butylphenyl)iodonium bis-perfluoroethane sulfonimide, from 3M Corporation, 0.46 g of DIPA 1 weight % in methyl-2-hydroxyisobutyrate (MHIB)) and 0.03 g of 10 weight % PGMEA solution of a surfactant (fluoroaliphatic polymeric ester, supplied by 3M Corporation, St. Paul Minn.) were dissolved in 23.872 of MHIB) to form a photoresist solution.

EXAMPLE 42

Example 40 was repeated with the photoresist from Example 41 and good results were obtained.

EXAMPLE 43

Example 37 was repeated with bis(triphenyl sulfonium) perfluoropropane-1,3-disulfonate from Example 2 replacing bis(triphenyl sulfonium)perfluorobutane-1,4-disulfonate to make a resist solution.

EXAMPLE 44

Example 37 was repeated with resist from Example 43 and good results were obtained.

EXAMPLE 45

Example 41 was repeated with bis triphenyl sulfonium perfluoropropane-1,3-disulfonate from Example 2 replacing bis(triphenyl sulfonium)perfluorobutane-1,4-disulfonate to make a resist solution.

EXAMPLE 46

Example 37 was repeated with resist from Example 45 and good results were obtained.

EXAMPLE 47

Example 37 was repeated with bis(4-t-butylphenyl iodonium)triphenyl sulfonium perfluorobutane-1,4-disulfonate from Example 3 replacing bis(triphenyl sulfonium)perfluorobutane-1,4-disulfonate to make a resist solution.

EXAMPLE 48

Example 38 was repeated with photoresist from Example 47 and good results were obtained.

EXAMPLE 49

Example 41 was repeated with bis(4-t-butylphenyl iodonium)triphenyl sulfonium perfluorobutane-1,4-disulfonate from Example 3 replacing bis(triphenyl sulfonium)perfluorobutane-1,4-disulfonate to make a resist solution.

EXAMPLE 50

Example 38 was repeated with resist from Example 49 and good results were obtained.

EXAMPLE 51

Example 37 was repeated with bis(benzoyltetramethylenesulfonium)perfluoropropane-1,3-disulfonate from Example 5 replacing bis(triphenyl sulfonium)perfluorobutane-1,4-disulfonate to make a resist solution.

EXAMPLE 52

Example 38 was repeated with resist from Example 51 and good results were obtained.

EXAMPLE 53

Example 41 was repeated with bis(benzoyltetramethylenesulfonium)perfluoropropane-1,3-disulfonate from Example 5 replacing bis(triphenyl sulfonium)perfluorobutane-1,4-disulfonate to make a resist solution.

EXAMPLE 54

Example 38 was repeated with resist from Example 49 and good results were obtained.

EXAMPLE 55

Example 39 can be repeated with triphenyl sulfonium bis-perfluoroethane sulfonamide in place of bis(4-t-butylphenyl) iodonium bis-perfluoroethane sulfonimide to form a resist solution.

EXAMPLE 56

Example 38 can be repeated with the resist of Example 55 and good results are expected.

EXAMPLE 57

Examples 37, 39, or 41 can be repeated with one of bis(4-t-butylphenyl iodonium)triphenyl sulfonium perfluoropropane-1,3-disulfonate, bis(Benzoyltetramethylene-sulfonium)perfluorobutane-1,4-disulfonate, bis(tris(4-t-butyl phenyl)sulfonium)perfluorobutane-1,4-disulfonate, bis(tris (4-t-butyl phenyl)sulfonium)perfluoropropane-1,3-disulfonate, bis(4-t-butylphenyl diphenyl sulfonium)perfluorobutane-1,4-disulfonate, bis(4-t-butylphenyl-diphenyl sulfonium)perfluoropropane-1,3-disulfonate, bis(triphenyl sulfonium)perfluoropropane-1-carboxylate-3-sulfonate, bis (triphenyl sulfonium)perfluorobutane-1 carboxylate-4-sulfonate, bis(4-t-butylphenyl iodonium)triphenyl sulfonium perfluoropropane-1-carboxylate-3-sulfonate, bis(4-t-butylphenyl iodonium)triphenyl sulfonium perfluorobutane-1-carboxylate-4-sulfonate, bis(Benzoyltetramethylene-sulfonium)perfluoropropane-1-carboxylate-3-sulfonate, bis (Benzoyltetramethylene-sulfonium)perfluorobutane-1-carboxylate-4-sulfonate, bis(tris(4-t-butyl phenyl)sulfonium)perfluoropropane-1-carboxylate-3-sulfonate, bis (tris(4-t-butyl phenyl)sulfonium)perfluorobutane-1-carboxylate-4-sulfonate, bis(4-t-butylphenyl diphenyl sulfonium)perfluoropropane-1-carboxylate-3-sulfonate, bis (4-t-butylphenyl diphenyl sulfonium)perfluorobutane-1-carboxylate-4-sulfonate, bis(4-t-butylphenyl iodonium)methane disulfonate, bis(triphenyl sulfonium)methane disulfonate, bis(4-t-butylphenyl iodonium)perfluoromethane disulfonate, bis(triphenyl sulfonium)perfluoromethane disulfonate, bis(4-t-butylphenyl iodonium)triphenyl sulfonium perfluoromethane disulfonate, bis(4-t-butylphenyl iodonium)triphenyl sulfonium methane disulfonate, bis(Benzoyltetramethylenesulfonium)perfluoromethane disulfonate, bis (Benzoyltetramethylene-sulfonium)methane disulfonate, bis (tris(4-t-butyl phenyl)sulfonium)perfluoromethane disulfonate, bis(tris(4-t-butyl phenyl)sulfonium)methane disulfonate, bis(4-t-butylphenyl diphenylsulfonium)perfluoromethane disulfonate, or bis(4-t-butylphenyl diphenylsulfonium)methane disulfonate, as well as the aforementioned inventive compounds mentioned herein, replacing bis(4-t-butylphenyl iodonium)methane disulfonate to make a resist solution.

EXAMPLE 58

Example 38 can be repeated with one of the resist solutions of Example 57 and good results are expected.

EXAMPLE 59

Examples 37, 39 or 41 can be repeated by substituting the polymer therein with one of the following polymers:

poly(2-methyl-2-adamantyl methacrylate-co-2-ethyl-2-adamantyl methacrylate-co-3-hydroxy-1-methacryloxyadamantane-co-α-gamma-butyrolactone methacrylate); poly(2-ethyl-2-adamantyl methacrylate-co-3-hydroxy-1-methacryloxyadamantane-co-β-gamma-butyrolactone methacrylate); poly(2-methyl-2-adamantyl methacrylate-co-3-hydroxy-1-methacryloxyadamantane-co-β-gamma-butyrolactone methacrylate); poly(t-butyl norbornene carboxylate-co-maleic anhydride-co-2-methyl-2-adamantyl methacrylate-co-β-gamma-butyrolactone methacrylate-co-methacryloyloxy norbornene methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca8-yl methacrylate); poly(2-ethyl-2-adamantyl methacrylate-co-3-hydroxy-1-adamantyl acrylate-co-β-gamma-butyrolactone methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-methyl-2-adamantyl methacrylate-co-3,5-dihydroxy-1-methacryloxyadamantane-co-α-gamma-butyrolactone methacrylate); poly (2-methyl-2-adamantyl methacrylate-co-3,5-dimethyl-7-hydroxy adamantyl methacrylate-co-α-gamma-butyrolactone methacrylate); poly(2-methyl-2-adamantyl acrylate-co-3-hydroxy-1-methacryloxyadamantane-co-α-gamma-butyrolactone methacrylate); poly(2-methyl-2-adamantyl methacrylate-co-3-hydroxy-1-methacryloxyadamantane-co-β-gamma-butyrolactone methacrylate-co-tricyclo-[5,2,1,0$^{2,6}$]deca8-yl methacrylate); poly(2-methyl-2-adamantyl methacrylate-co-α-gamma-butyrolactone methacrylate-co-3-hydroxy-1-methacryloxyadamantane-co-ethylcyclopentylacrylate); poly(2-methyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-methacryloxyadamantane-co-α-gamma-butyrolactone methacrylate-co-2-ethyl-2-adamantyl methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca8-yl methacrylate); poly(2-methyl-2-adamantyl methacrylate-co-2-ethyl-2-adamantyl methacrylate-co-β-gamma-butyrolactone methacrylate-co-3-hydroxy-1-methacryloxyadamantane); poly(2-methyl-2-adamantyl methacrylate-co-2-ethyl-2-adamantyl methacrylate-co-α-gamma-butyrolactone methacrylate-co-3-hydroxy-1-methacryloxyadamantane); poly(2-methyl-2-adamantyl methacrylate-co-methacryloyloxy norbornene methacrylate-co-β-gamma-butyrolactone methacrylate); poly(ethylcyclopentylmethacrylate-co-2-ethyl-2-adamantyl methacrylate-co-α-gamma-butyrolactone acrylate); poly(2-ethyl-2-adamantyl methacrylate-co-3-hydroxy-1-adamantyl acrylate-co-isobutyl methacrylate-co-α-gamma-butyrolactone acrylate); poly(2-methyl-2-adamantyl methacrylate-co-β-gamma-butyrolactone methacrylate-co-3-hydroxy-1-adamantyl acrylate-co-tricyclo[5,2,1,02,6]-deca-8-yl methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-βgamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-β-gamma-butyrolactone methacrylate-co-2-adamantyl methacrylate-co-3-hydroxy-1-methacryloxyadamatane); poly(2-methyl-2-adamantyl methacrylate-co-methacryloyloxy norbornene methacrylate-co-tricyclo-[5,2,1,02,6]deca-8-yl methacrylate-co-3-hydroxy-1-methacryloxyadamatane-co-αgamma-butyrolactone methacrylate); poly(2-ethyl-2-adamantyl methacrylate-co-3-hydroxy-1-adamantyl acrylate-co-tricyclo[5,2,1,02,6] deca-8-yl methacrylate-co-αgamma-butyrolactone methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-3-hydroxy-1-methacryloxyadamatane-co-α-gamma-butyrolactone methacrylate-co-2-ethyl-2-adamantyl-co-methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-α-gamma-butyrolactone methacrylate-co-2-adamantyl methacrylate); poly(2-ethyl-2-adamantyl methacrylate-co-3-hydroxy-1-adamantyl acrylate-co-α-gamma-butyrolactone methacrylate); and poly(2-ethyl-2-adamantyl methacrylate-co-3-hydroxy-1-adamantyl acrylate-co-α-gamma-butyrolactone acrylate-co-tricyclo[5,2,1,02,6]deca-8-yl methacrylate) to form a photoresist solution.

EXAMPLE 60

Example 38 can be repeated with a resist formed in Example 59 and good results are expected.

EXAMPLE 61

Example 59 can be repeated by replacing bis(triphenyl sulfonium)perfluorobutane-1,4-disulfonate with one of bis(triphenyl sulfonium)perfluoropropane-1,3-disulfonate, bis(4-t-butylphenyl iodonium)triphenyl sulfonium perfluorobutane-1,4-disulfonate, bis(4-t-butylphenyl iodonium)triphenyl sulfonium perfluoropropane-1,3-disulfonate, bis(4-t-butylphenyl iodonium)triphenyl sulfonium perfluoropropane-1,3-disulfonate, bis(4-t-butylphenyl iodonium)triphenyl sulfonium perfluoropropane-1,3-disulfonate, bis(Benzoyltetramethylenesulfonium)perfluorobutane-1,4-disulfonate, bis(tris(4-t-butyl phenyl)sulfonium)perfluorobutane-1,4-disulfonate, bis(tris(4-t-butyl phenyl)sulfonium)perfluoropropane-1,3-disulfonate, bis(4-t-butylphenyl diphenyl sulfonium)perfluorobutane-1,4-disulfonate, bis(4-t-butylphenyl diphenyl sulfonium)perfluoropropane-1,3-disulfonate, bis(triphenyl sulfonium)perfluoropropane-1-carboxylate-3-sulfonate, bis(triphenyl sulfonium)perfluorobutane-1-carboxylate-4-sulfonate bis(4-t-butylphenyl iodonium)triphenyl sulfonium perfluoropropane-1-carboxylate-3-sulfonate, bis(4-t-butylphenyl iodonium)triphenyl sulfonium perfluorobutane-1-carboxylate-4-sulfonate, bis(Benzoyltetramethylenesulfonium)perfluoropropane-1-carboxylate-3-sulfonate, bis(Benzoyltetramethylenesulfonium)perfluorobutane-1-carboxylate-4-sulfonate, bis(tris(4-t-butyl phenyl)sulfonium)perfluoropropane-1-carboxylate-3-sulfonate, bis(tris(4-t-butyl phenyl)sulfonium)perfluorobutane-1-carboxylate-4-sulfonate, bis(4-t-butylphenyl diphenyl sulfonium)perfluoropropane-1-carboxylate-3-sulfonate, bis(4-t-butylphenyl diphenyl sulfonium)perfluorobutane-1-carboxylate-4-sulfonate, bis(4-t-butylphenyl iodonium)methane disulfonate, bis(triphenyl sulfonium)methane disulfonate, bis(4-t-butylphenyl iodonium)perfluoromethane disulfonate, bis(triphenyl sulfonium)perfluoromethane disulfonate, bis(4-t-butylphenyl iodonium)triphenyl sulfonium perfluoromethane disulfonate, bis(4-t-butylphenyl iodonium)triphenyl sulfonium methane disulfonate, bis(Benzoyltetramethylenesulfonium)perfluoromethane disulfonate, bis(Benzoyltetramethylenesulfonium)methane disulfonate, bis(tris(4-t-butyl phenyl)sulfonium)perfluoromethane disulfonate, bis(tris(4-t-butyl phenyl)sulfonium)methane disulfonate, bis(4-t-butylphenyl diphenylsulfonium)perfluoromethane disulfonate, or bis(4-t-butylphenyl diphenylsulfonium)methane disulfonate to form a resist solution.

EXAMPLE 62

Example 38 can be repeated with a resist formed in Example 61 and good results are expected.

We claim:

1. A photoresist composition useful for imaging in deep UV comprising;
   a) a polymer containing an acid labile group; and,
   b) a compound of the formula

A-X—B (i) where A-X—B form an ionic compound Ai Xi Bi,
where Ai and Bi are each individually an organic onium cation; and
Xi is anion of the formula

Q-R$_{500}$—SO$_3^-$ where
Q is selected from $^-O_3S$ and $^-O_2C$; and
R$_{500}$ is a group selected from linear or branched alkyl, cycloalkyl, aryl, or combinations thereof, optionally containing a catenary S or N, where the alkyl, cycloalkyl, and aryl groups are unsubstituted or substituted by one or more groups selected from the group consisting of halogen, unsubstituted or substituted alkyl, unsubstituted or substituted $C_{1-8}$ perfluoroalkyl, hydroxyl, cyano, sulfate, and nitro; and
where the organic onium cation is selected from

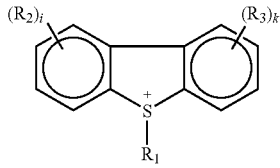

and

Y—Ar where Ar is selected from

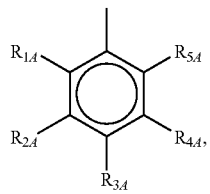

naphthyl, or anthryl;
Y is selected from

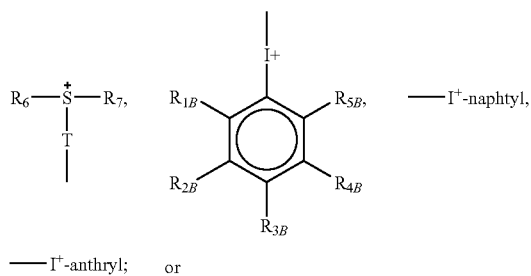

—I$^+$-anthryl; or (ii) where A-X—B form a non-ionic compound Ac-Xc-Bc, where Ac and Bc are each individually selected from —SO$_2$—(C(X2)$_2$)$_m$—R$_{600}$, —O—CMX3-R$_{700}$,
—C(=N$_2$)—SO$_2$—R$_{600}$, and

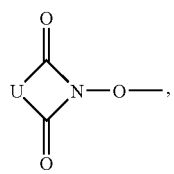

where R$_{600}$ is selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, or

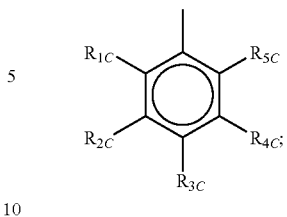

where R$_{700}$ is selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, or

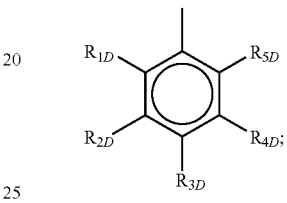

U is $C_1$ to $C_4$ unsubstituted or substituted alkylene;
Xc is

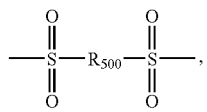

where R$_{500}$ is defined above;
where R$_1$, R$_2$, R$_3$, R$_{1A}$, R$_{1B}$, R$_{1C}$, R$_{2A}$, R$_{2B}$, R$_{2C}$, R$_{2D}$, R$_{3A}$, R$_{3B}$, R$_{3C}$, R$_{3D}$, R$_{4A}$, R$_{4B}$, R$_{4C}$, R$_{4D}$, R$_{5A}$, R$_{5B}$ and R$_{5C}$ are each independently selected from Z, hydrogen, OSO$_2$R$_9$, OR$_{20}$, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, arylcarbonylmethyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, straight or branched perfluoroalkyl, monocycloperfluoroalkyl or polycycloperfluoroalkyl, straight or branched alkoxy chain, nitro, cyano, halogen, carboxyl, hydroxyl, sulfate, tresyl, or hydroxyl; either (i) one of R$_{1D}$ or R$_{5D}$ is nitro with the other being selected from hydrogen, straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, cyano, or hydroxyl or (ii) both of R$_{1D}$ and R$_{5D}$ are nitro;
R$_6$ and R$_7$ are each independently selected from straight or branched alkyl chain optionally containing one or more O atoms, monocycloalkyl or polycycloalkyl group optionally containing one or more O atoms, monocycloalkyl- or polycycloalkylcarbonyl group, aryl, aralkyl, straight or branched perfluoroalkyl, monocycloperfluoroalkyl or polycycloperfluoroalkyl, arylcarbonylmethyl group, nitro, cyano, or hydroxyl or $R_6$ and $R_7$ together with the S atom to which they are attached form a 5-, 6-, or 7-membered saturated or unsaturated ring optionally containing one or more O atoms;

$R_9$ is selected from alkyl, fluoroalkyl, perfluoroalkyl, aryl, fluoroaryl, perfluoroaryl, monocycloalkyl or polycycloalkyl group with the cycloalkyl ring optionally containing one or more O atoms, monocyclofluoroalkyl or polycyclofluoroalkyl group with the cycloalkyl ring optionally containing one or more O atoms, or monocycloperfluoralkyl or polycycloperfluoroalkyl group with the cycloalkyl ring optionally containing one or more O atoms;

$R_{20}$ is alkoxyalkyl, alkoxycarbonylalkyl, alkylcarbonyl, monocycloalkyl- or polycycloalkyloxycarbonylalkyl with the cycloalkyl ring optionally containing one or more O atoms, or monocycloalkyl- or polycycloalkyloxyalkyl with the cycloalkyl ring optionally containing one or more O atoms;

T is a direct bond, a divalent straight or branched alkyl group optionally containing one or more O atoms, divalent aryl group, divalent aralkyl group, or divalent monocycloalkyl or polycycloalkyl group optionally containing one or more O atoms;

Z is -(V)$_j$—(C(X11)(X12))$_n$-O—C(=O)—R$_8$, where either (i) one of X11 or X12 is straight or branched alkyl chain containing at least one fluorine atom and the other is hydrogen, halogen, or straight or branched alkyl chain or (ii) both of X11 and X12 are straight or branched alkyl chain containing at least one fluorine atom;

V is a linkage group selected from a direct bond, a divalent straight or branched alkyl group optionally containing one or more O atoms, divalent aryl group, divalent aralkyl group, or divalent monocycloalkyl or polycycloalkyl group optionally containing one or more O atoms;

X2 is hydrogen, halogen, or straight or branched alkyl chain optionally containing one or more O atoms;

$R_5$ is a straight or branched alkyl chain optionally containing one or more O atoms, a monocycloalkyl or polycycloalkyl group optionally containing one or more O atoms, or aryl;

X3 is hydrogen, straight or branched alkyl chain, halogen, cyano, or —C(=O)—R$_{50}$ where $R_{50}$ is selected from straight or branched alkyl chain optionally containing one or more O atoms or —O—R$_{51}$ where $R_{51}$ is hydrogen or straight or branched alkyl chain;

each of i and k are independently 0 or a positive integer;

j is 0 to 10;

m is 0 to 10;

and n is 0 to 10, the straight or branched alkyl chain optionally containing one or more O atoms, straight or branched alkyl chain, straight or branched alkoxy chain, monocycloalkyl or polycycloalkyl group optionally containing one or more O atoms, monocycloalkyl- or polycycloalkylcarbonyl group, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, aralkyl, aryl, naphthyl, anthryl, 5-, 6-, or 7-membered saturated or unsaturated ring optionally containing one or more O atoms, or arylcarbonylmethyl group being unsubstituted or substituted by one or more groups selected from the group consisting of Z, halogen, alkyl, $C_{1-8}$ perfluoroalkyl, monocycloalkyl or polycycloalkyl, OR$_{20}$, alkoxy, $C_{3-20}$ cyclic alkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

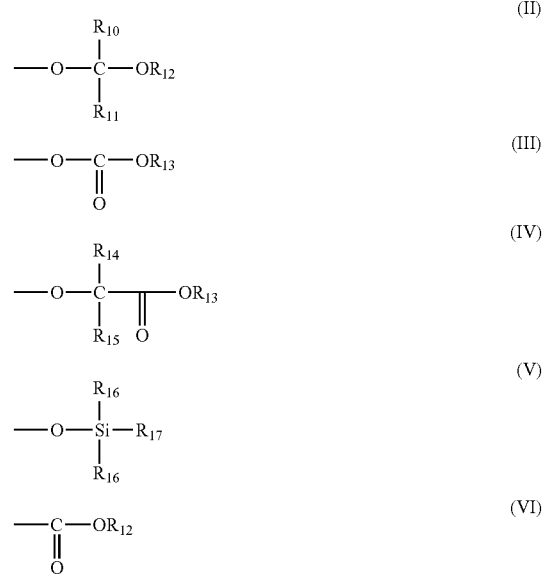

wherein $R_{10}$ and $R_{11}$ each independently represent a hydrogen atom, a straight or branched alkyl chain optionally containing one or more O atoms, or a monocycloalkyl or polycycloalkyl group optionally containing one or more O atoms, or $R_{10}$ and $R_{11}$ together can represent an alkylene group to form a five- or six-membered ring;

$R_{12}$ represents a straight or branched alkyl chain optionally containing one or more O atoms, a monocycloalkyl or polycycloalkyl group optionally containing one or more O atoms, or aralkyl, or $R_{10}$ and $R_{12}$ together represent an alkylene group which forms a five- or six-membered ring together with the interposing —C—O— group, the carbon atom in the ring being optionally substituted by an oxygen atom;

$R_{13}$ represents a straight or branched alkyl chain optionally containing one or more O atoms or a monocycloalkyl or polycycloalkyl group optionally containing one or more O atoms;

$R_{14}$ and $R_{15}$ each independently represent a hydrogen atom, a straight or branched alkyl chain optionally containing one or more O atoms or a monocycloalkyl or polycycloalkyl group optionally containing one or more O atoms;

$R_{16}$ represents a straight or branched alkyl chain optionally containing one or more O atoms, a monocycloalkyl or polycycloalkyl group optionally containing one or more O atoms, aryl, or aralkyl; and $R_{17}$ represents straight or branched alkyl chain optionally containing one or more O atoms, a monocycloalkyl or polycycloalkyl group optionally containing one or more O atoms, aryl, aralkyl, the group —Si($R_{16}$)$_2R_{17}$, or the group —O—Si($R_{16}$)$_2R_{17}$, the straight or branched alkyl chain optionally containing one or more O atoms, monocycloalkyl or polycycloalkyl group optionally containing one or more O atoms, aryl, and aralkyl being unsubstituted or substituted as above.

2. The composition of claim 1, wherein for b) the compound is Ai Xi Bi.

3. The composition of claim 2 wherein for b), each of Ai and Bi are selected from

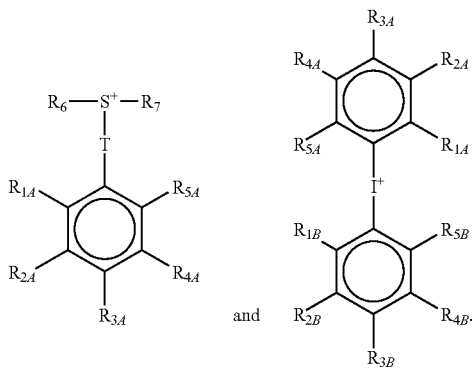

and

4. The composition of claim 2 wherein for b), Ai and Bi are each

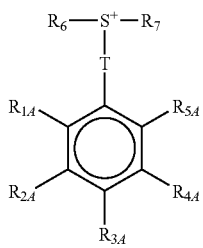

where $R_6$ and $R_7$ are each independently unsubstituted or substituted aryl, or $R_6$ and $R_7$ together with the S atom to which they are attached form a 5-, 6-, or 7-membered saturated or unsaturated ring optionally containing one or more O atoms; T is a direct bond or a divalent straight or branched alkyl group optionally containing one or more O atoms optionally substituted with oxo, and $R_{500}$ is linear or branched alkyl unsubstituted or substituted by one or more halogen groups.

5. The composition of claim 1 wherein for b), Ai is

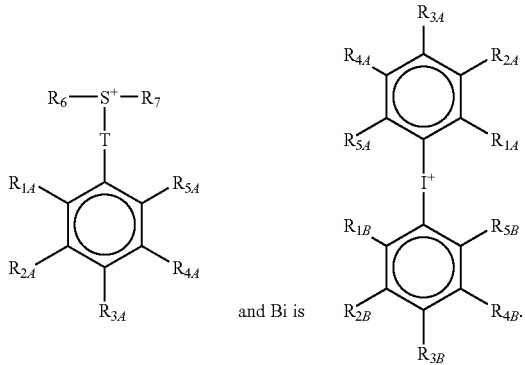

and Bi is

6. The composition of claim 1 wherein for b), the compound is selected from the group bis(4-t-butylphenyl iodonium)triphenyl sulfonium perfluorobutane-1,4-disulfonate, bis(4-t-butylphenyl iodonium)triphenyl sulfonium perfluoropropane-1,3-disulfonate, bis(4-t-butylphenyl iodonium)triphenyl sulfonium perfluoropropane-1-carboxylate-3-sulfonate, bis(4-t-butylphenyl iodonium)triphenyl sulfonium perfluorobutane-1-carboxylate-4-sulfonate, bis(4-t-butylphenyl iodonium)triphenyl sulfonium perfluoromethane disulfonate, bis(4-t-butylphenyl iodonium)triphenyl sulfonium methane disulfonate, bis(4-t-butylphenyl iodonium)triphenyl sulfonium perfluoroethane disulfonate, bis(4-t-butylphenyl iodonium)triphenyl sulfonium ethane disulfonate, bis(triphenyl sulfonium)perfluorobutane-1,4-disulfonate, bis(triphenyl sulfonium)perfluoropropane-1,3-disulfonate, bis(benzoyltetramethylene-sulfonium)perfluoropropane-1,3-disulfonate, bis(benzoyltetramethylenesulfonium)perfluorobutane-1,4-disulfonate, bis(tris(4-t-butyl phenyl)sulfonium) perfluorobutane-1,4-disulfonate, bis(tris(4-t-butyl phenyl) sulfonium)perfluorobutane-1,4-disulfonate, bis(tris(4-t-butyl phenyl)sulfonium)perfluoropropane-1,3-disulfonate, bis(tris(4-t-butyl phenyl)sulfonium)perfluoropropane-1,3-disulfonate, bis(4-t-butylphenyl diphenyl sulfonium)perfluorobutane-1,4-disulfonate, bis(4-t-butylphenyl diphenyl sulfonium)perfluoropropane-1,3-disulfonate, bis(triphenyl sulfonium)perfluoropropane-1-carboxylate-3-sulfonate, bis(biphenyl sulfonium)perfluorobutane-1-carboxylate-4-sulfonate, bis(benzoyltetramethylenesulfonium)perfluoropropane-1-carboxylate-3-sulfonate, bis(benzoyltetramethylenesulfonium)perfluorobutane-1-carboxylate-4-sulfonate, bis(tris(4-t-butyl phenyl) sulfonium)perfluoropropane-1-carboxylate-3-sulfonate, bis(tris(4-t-butyl phenyl)sulfonium)perfluorobutane-1-carboxylate-4-sulfonate, bis(4-t-butylphenyl diphenyl sulfonium)perfluoropropane-1-carboxylate-3-sulfonate, bis(4-t-butylphenyl diphenyl sulfonium)perfluorobutane-1-carboxylate-4-sulfonate, bis(4-t-butyl phenyl iodonium)methane disulfonate, bis(biphenyl sulfonium)methane disulfonate, bis(4-t-butylphenyl iodonium)perfluoromethane disulfonate, bis(triphenyl sulfonium)perfluoromethane disulfonate, bis(benzoyltetramethylene-sulfonium)perfluoromethane disulfonate, bis(benzoyltetramethylenesulfonium)methane disulfonate, bis(tris(4-t-butyl phenyl) sulfonium)perfluoromethane disulfonate, bis(tris(4-t-butyl phenyl)sulfonium)methane disulfonate, bis(4-t-butylphenyl diphenylsulfonium)perfluoromethane disulfonate, bis(4-t-butylphenyl diphenylsulfonium)methane disulfonate, bis(4-octyloxyphenyl)iodonium perfluorobutane-1,4-disulfonate, bis(4-octyloxyphenyl)iodonium ethane disulfonate, bis(4-octyloxyphenyl)iodonium perfluoroethane disulfonate, bis(4-octyloxyphenyl)iodonium perfluoropropane-1,3-disulfonate, bis(4-octyloxyphenyl)iodonium perfluoropropane-1-carboxylate-3-sulfonate, bis(4-octyloxyphenyl)iodonium perfluorobutane-1-carboxylate-4-sulfonate, bis(4-octyloxyphenyl)iodonium methane disulfonate, bis(4-octyloxyphenyl)iodonium perfluoromethane disulfonate, bis(4-octyloxyphenyl)phenyl sulfonium perfluorobutane-1,4-disulfonate, bis(4-octyloxyphenyl)phenyl sulfonium ethane disulfonate, bis(4-octyloxyphenyl)phenyl sulfonium perfluoroethane disulfonate, bis(4-octyloxyphenyl)phenyl sulfonium perfluoropropane-1,3-disulfonate, bis(4-octyloxyphenyl)phenyl sulfonium perfluoropropane-1-carboxylate-3-sulfonate, bis(4-octyloxyphenyl)phenyl sulfonium perfluorobutane-1-carboxylate-4-sulfonate, bis(4-octyloxyphenyl)phenyl sulfonium methane disulfonate, bis(4-octyloxyphenyl)phenyl sulfonium perfluoromethane disulfonate, bis[bis[4-pentafluorobenzene-sulfonyloxy-phenyl]phenylsulfonium]perfluorobutane-1,4-disulfonate, bis[bis[4-pentafluorobenzene-sulfonyloxyphenyl]phenylsulfonium]ethane disulfonate, bis[bis[4-pentafluorobenzenesulfonyloxyphenyl]phenylsulfonium]perfluoroethane disulfonate, bis[bis[4-pentafluorobenzenesulfonyloxyphenyl]phenylsulfonium]perfluoropropane-1,3-disulfonate, bis[bis[4-pentafluorobenzenesulfonyloxyphenyl]phenylsulfonium]perfluoropropane-1-carboxylate-3-sulfonate, bis[bis[4-pentafluorobenzenesulfonyl-oxyphenyl]phenylsulfonium]perfluorobutane-1-carboxylate-4-sulfonate, bis[bis[4-pentafluorobenzenesulfonyloxyphenyl]phenylsulfonium]methane disulfonate, bis[bis[4-pentafluorobenzenesulfonyloxyphenyl]phenylsulfonium]perfluoromethane disulfonate, bis[bis[4-(3,5-di(trifluoromethyl)benzenesulfonyloxy)-phenyl]phenylsulfonium]perfluorobutane-1,4-disulfonate, bis[bis[4-(3,5-di(trifluoromethyl)-benzenesulfonyloxy)phenyl]phenylsulfonium]ethane disulfonate, bis[bis[4-(3,5-di(trifluoromethyl)benzenesulfonyloxy)phenyl]phenylsulfonium]perfluoroethane disulfonate, bis[bis[4-(3,5-di(trifluoromethyl)benzenesulfonyloxy)phenyl]phenylsulfonium]perfluoropropane-1,3-disulfonate, bis[bis[4-(3,5-di(trifluoromethyl)-benzenesulfonyloxy)phenyl]phenylsulfonium]perfluoropropane-1-carboxylate-3-sulfonate, bis[bis[4-(3,5-di(trifluoromethyl)benzenesulfonyloxy)phenyl]phenylsulfonium]perfluorobutane-1-carboxylate-4-sulfonate, bis[bis[4-(3,5-di(trifluoromethyl)benzenesulfonyloxy)-phenyl]phenylsulfonium]methane disulfonate, bis(4-t-butylphenyl iodonium)ethane disulfonate, bis(4-t-butylphenyl iodonium)perfluoroethane disulfonate, bis(triphenyl sulfonium)ethane disulfonate, bis(triphenyl sulfonium)perfluoroethane disulfonate, bis(benzoyltetramethylenesulfonium)perfluoroethane disulfonate, bis(benzoyltetramethylenesulfonium)ethane disulfonate, bis(tris(4-t-butyl phenyl)sulfonium)perfluoroethane disulfonate, bis(tris(4-t-butyl phenyl)sulfonium)ethane disulfonate, bis(4-t-butylphenyl diphenylsulfonium)perfluoroethane disulfonate, and bis(4-t-butylphenyl diphenylsulfonium)ethane disulfonate.

7. The composition of claim 1 which further comprises c) a second photoacid generator Ai Xi1 where Ai is as defined above and Xi1 is an anion selected from $CF_3SO_3^-$, $CHF_2SO_3^-$, $CH_3SO_3^-$, $CCl_3SO_3^-$, $C_2F_5SO_3^-$, $C2HF_4SO_3^-$, $C_4F_9SO_3^-$, camphor sulfonate, perfluorooctane sulfonate, benzene sulfonate, pentafluorobenzene sulfonate, toluene sulfonate, perfluorotoluene sulfonate, $(Rf1SO_2)_3C^-$ and $(Rf1SO_2)_2N^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and Rg-O—Rf2-$SO_3^-$, where Rf2 is selected from the group consisting of linear or branched $(CF_2)_j$ where j is an integer from 4 to 10 and $C_1$-$C_{12}$ cycloperfluoroalkyl divalent radical which is optionally perfluoro$C_{1-10}$alkyl substituted, Rg is selected from the group consisting of $C_1$-$C_{20}$ linear, branched, monocycloalkyl or polycycloalkyl, $C_1$-$C_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated.

8. The composition of claim 7 wherein Ai is selected from

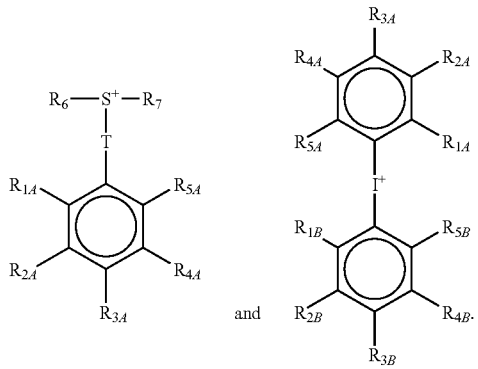

9. The composition of claim 8 wherein the anion Xi1 is selected from include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)_2(C_4F_9SO_2)C^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)(C_4F_9SO_2)N^-$, $[(CF_3)_2NC_2F_4SO_2]_2N^-$, $(CF_3)_2NC_2F_4SO_2C^-(SO_2CF_3)_2$, $(3,5-bis(CF_3)C_6H_3)SO_2N^-SO_2CF_3$, $C_6F_5SO_2C^-(SO_2CF_3)_2$, $C_6F_5SO_2N^-SO_2CF_3$,

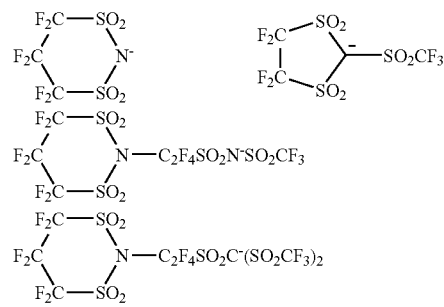

$CF_3CHFO(CF_2)_4SO_3^-$, $CF_3CH_2O(CF_2)_4SO_3^-$, $CH_3CH_2O(CF_2)_4SO_3^-$, $CH_3CH_2CH_2O(CF_2)_4SO_3^-$, $CH_3O(CF_2)_4SO_3^-$, $C_2H_5O(CF_2)_4SO_3^-$, $C_4H_9O(CF_2)_4SO_3^-$, $C_6H_5CH_2O(CF_2)_4SO_3^-$, $C_2H_5OCF_2CF(CF_3)SO_3^-$, $CH_2=CHCH_2O(CF_2)_4SO_3^-$, $CH_3OCF_2CF(CF_3)SO_3^-$, $C_4H_9OCF_2CF(CF_3)SO_3^-$, $C_8H_{17}O(CF_2)_2SO_3^-$, and $C_4H_9O(CF_2)_2SO_3^-$.

10. A process for imaging a photoresist comprising the steps of: include
   a) coating a substrate with the composition of claim 1;
   b) baking the substrate to substantially remove the solvent;
   c) image-wise exposing the photoresist coating;
   d) postexposure baking the photoresist coating; and
   e) developing the photoresist coating with an aqueous alkaline solution.

* * * * *